US005451453A

United States Patent [19]

Gagnon et al.

[11] Patent Number: 5,451,453
[45] Date of Patent: Sep. 19, 1995

[54] SUPPORTS HAVING AZLACTONE-FUNCTIONAL SURFACES, ADDUCT SUPPORTS, AND METHODS OF PREPARING BOTH

[75] Inventors: David R. Gagnon, St. Paul; Patrick L. Coleman, Minneapolis; Gary J. Drtina; Oh-Seung Kwon, both of Woodbury; Christopher S. Lyons, St. Paul; Dean S. Milbrath, West Lakeland; Jerald K. Rasmussen, May Township; Julie B. Stahl, St. Paul, all of Minn.

[73] Assignee: Minnesota Mining and Manufacturing Company, St. Paul, Minn.

[21] Appl. No.: 262,738

[22] Filed: Jun. 20, 1994

Related U.S. Application Data

[62] Division of Ser. No. 896,107, Jun. 9, 1992, Pat. No. 5,344,701.

[51] Int. Cl.$^6$ ............... C08F 20/58; C08F 26/06; B01J 20/28; B32B 3/26
[52] U.S. Cl. ............... 428/305.5; 428/304.4; 428/308.4; 428/315.5; 428/319.3; 522/87; 522/88; 522/89; 522/116; 522/136; 522/138; 525/54.1; 525/63; 525/279; 525/300
[58] Field of Search ............... 428/304.4, 308.4, 308.8, 428/315.5, 319.3; 522/116, 136, 173, 87, 88, 89, 138; 525/54.1, 63, 279, 300

[56] References Cited

U.S. PATENT DOCUMENTS 3,488,327  1/1970  Kollinsky et al. ............... 260/78.3

(List continued on next page.)

FOREIGN PATENT DOCUMENTS

| 32615/68 | 7/1969 | Australia . | |
|---|---|---|---|
| 0264804 | 4/1988 | European Pat. Off. | C12N 11/00 |
| 0336762 | 10/1989 | European Pat. Off. | C08F 8/30 |
| 0392735 | 10/1990 | European Pat. Off. | C08F 8/48 |
| 0392783 | 10/1990 | European Pat. Off. | C08F 255/00 |
| 0407580 | 1/1991 | European Pat. Off. | A61L 33/00 |
| 0441660 | 8/1991 | European Pat. Off. | B01D 71/56 |
| 0467639 | 1/1992 | European Pat. Off. | B29C 59/14 |
| 2199946 | 7/1988 | United Kingdom | G01N 33/545 |
| WO92/07640 | 5/1992 | WIPO | B01D 63/02 |
| WO92/07899 | 5/1992 | WIPO | C08J 7/04 |
| WO93/06925 | 4/1993 | WIPO | B01J 20/28 |

OTHER PUBLICATIONS

Coleman et al., Journal of Chromatography, "Immobilization of Protein A at high density of azlactone-functional polymeric beads and their use in affinity chromatography", John Wiley, pp. 345–363 (1990).
Shkolnik et al., Journal of Applied Polymer Science, vol. 27, John Wiley, pp. 2189–2196 (1982).
Hsiue et al., Journal of Applied Polymer Science, vol. 30, John Wiley, pp. 1023–1033 (1985).
"Polyazlactones", Encyclopedia of Polymer Science and Engineering, vol. 11, John Wiley, pp. 558–571 (1988).

*Primary Examiner*—Susan Berman
*Attorney, Agent, or Firm*—Gary L. Griswold; Walter N. Kirn; John H. Hornickel

[57] ABSTRACT

Supports having azlactone-functional surfaces, adduct supports prepared from such azlactone-functional supports, and methods of preparing both are disclosed. Azlactone functionality is introduced to surfaces of a pre-existing support in a manner which retains useful physical and chemical characteristics of the pre-existing support. One method involves exposing surfaces with high energy radiation to generate free radical reaction sites on the surfaces and causing azlactone-functional moieties to react with the free radical reaction sites. Another method involves coating surfaces with azlactone monomers, crosslinking monomers, and optionally co-monomers and polymerizing the monomers to form a polymerized coating of azlactone-functionality on the surfaces. Another method involves dispersion polymerization of azlactone-functional moieties to produce azlactone-functional particles within pores and interstices of a pre-existing support. Adduct supports are formed by coupling nucleophilic reagents, such as biologically active materials, to azlactone-functional moieties of the support.

10 Claims, No Drawings

U.S. PATENT DOCUMENTS

| | | | |
|---|---|---|---|
| 3,583,950 | 6/1971 | Kollinsky et al. | 260/78 |
| 3,598,790 | 8/1971 | Kollinsky et al. | 260/78.3 |
| 3,634,218 | 1/1972 | Gotohda et al. | 204/159.17 |
| 3,941,718 | 3/1976 | Barabas et al. | 252/430 |
| 4,045,353 | 8/1977 | Kosaka et al. | 210/502 |
| 4,280,970 | 7/1981 | Kesting | 264/1.7 |
| 4,304,705 | 12/1981 | Heilmann et al. | 260/30.4 |
| 4,340,479 | 7/1982 | Pall | 210/490 |
| 4,407,846 | 10/1983 | Machi et al. | 427/35 |
| 4,451,619 | 5/1984 | Heilmann et al. | 525/379 |
| 4,563,388 | 1/1986 | Bonk et al. | 428/304.4 |
| 4,595,726 | 6/1986 | Klosiewicz | 525/71 |
| 4,605,685 | 8/1986 | Momose et al. | 522/124 |
| 4,613,665 | 9/1986 | Larm | 536/20 |
| 4,693,985 | 9/1987 | Degen et al. | 436/531 |
| 4,695,608 | 9/1987 | Engler et al. | 525/308 |
| 4,705,753 | 11/1987 | Gregor et al. | 435/180 |
| 4,726,989 | 2/1988 | Mrozinski | 428/315.5 |
| 4,737,560 | 4/1988 | Heilmann et al. | 526/304 |
| 4,777,276 | 10/1988 | Rasmussen et al. | 556/419 |
| 4,824,870 | 4/1989 | Pemawansa et al. | 521/53 |
| 4,855,234 | 8/1989 | Hendrickson et al. | 435/181 |
| 4,871,824 | 10/1989 | Heilmann et al. | 526/304 |
| 4,914,223 | 4/1990 | Rasmussen et al. | 560/49 |
| 4,950,549 | 8/1990 | Rolando et al. | 428/500 |
| 4,961,954 | 10/1990 | Goldberg et al. | 427/2 |
| 4,963,494 | 10/1990 | Hibino et al. | 435/288 |
| 4,979,959 | 12/1990 | Guire | 623/66 |
| 4,981,798 | 1/1991 | Kamakura et al. | 435/179 |
| 4,981,933 | 1/1991 | Fazio et al. | 526/260 |
| 5,013,795 | 5/1991 | Coleman et al. | 525/279 |
| 5,037,656 | 8/1991 | Pitt et al. | 424/443 |
| 5,041,225 | 8/1991 | Norman | 210/500.36 |
| 5,059,654 | 10/1991 | Hou et al. | 525/54.1 |
| 5,071,880 | 12/1991 | Sugo et al. | 521/27 |
| 5,081,197 | 1/1992 | Heilmann et al. | 526/260 |
| 5,155,144 | 10/1992 | Manganaro et al. | 523/134 |
| 5,292,514 | 3/1994 | Capecchi et al. | 424/422 |
| 5,292,840 | 3/1994 | Heilmann et al. | 526/304 |
| 5,344,560 | 9/1994 | Sugo et al. | 210/500.23 |

SUPPORTS HAVING AZLACTONE-FUNCTIONAL SURFACES, ADDUCT SUPPORTS, AND METHODS OF PREPARING BOTH

This is a division of application Ser. No. 07/896,107 filed Jun. 9, 1992 now U.S. Pat. No. 5,344,701.

FIELD OF THE INVENTION

This patent application relates to supports having azlactone-functional surfaces, adduct supports prepared from such azlactone-functional supports, and methods of preparing both.

BACKGROUND OF THE INVENTION

Azlactone-functional polymeric supports have been prepared according to the methods disclosed in European Patent Publication 0 392 783 (Coleman et al.) and in European Patent Publication 0 392 735 (Heilmann et al.). In both of these publications, examples show methods of preparation which involve the homopolymerization or copolymerization of azlactone-functional polymers to become the polymeric support.

Azlactone-functional moieties are expensive and valuable. Preparation techniques which cause azlactone-functional moieties to be occluded from accessible use needlessly wastes the valuable azlactone functionality.

Also, there is a desire to place azlactone-functionality only at surfaces of a support where chemical or physical interaction with other materials, particularly biologically active materials can occur. Process IV described in European Patent Publication 0 392 735 discloses a method for coating azlactone-containing polymer at surfaces of substrates. Also, European Patent Publication 0 392 735 within the disclosure of Process IV and in Example 22 thereof identifies a desire to employ azlactone-containing monomers in the coating process to polymerize the monomer(s) in place.

There are a myriad of supports which have specific geometries useful for physical interaction with materials, particularly biologically active materials. These supports have specific physical and chemical characteristics: porosity, surface area, permeability, solvent resistance, hydrophilicity, flexibility, mechanical integrity, and other stability or feature in the use environment, etc., which must be retained for a pre-existing support to remain useful. For example, a microporous membrane will not remain useful as a filter if its porosity is harmfully compromised by the addition of an azlactone-functional moiety to its surfaces.

Monomeric 2-alkenyl-1,3-oxazolin-5-ones (which compounds and homologs thereof are referred to herein as 2-alkenyl azlactones) and copolymers thereof are known. Copolymers of 2-alkenyl azlactones and olefinically unsaturated monomers and coatings thereof are disclosed in U.S. Pat. No. 3,583,950 (Kollinsky et al.). Also, copolymers consisting essentially of a 2-alkenyl azlactone and an acrylic acid ester, and copolymerization thereof with vinylidene compounds having at least one hydroxyl group are disclosed in U.S. Pat. Nos. 3,488,327 and 3,598,790 (both to Kollinsky et al.). U.S. Pat. No. 4,695,608 (Engler et al.) discloses a bulk polymerization process for free radical polymerization of a vinyl monomer and a monomeric alkenyl azlactone or a macromolecular monomer with a molecular weight of less than about 30,000 in a wiped surface reactor such as a twin-screw extruder. Free radical initiator systems comprising a combination of reagents are useful in the process. Incorporation of alkenyl azlactones into acrylate pressure-sensitive adhesives improves the adhesives. Also disclosed in this patent are methods of preparation of 2-alkenyl azlactone monomers.

SUMMARY OF THE INVENTION

This invention provides azlactone-functional surfaces on a pre-existing support and methods of preparing such surfaces in a manner which retains useful physical and chemical characteristics of the pre-existing support. This invention also provides an adduct support prepared from such azlactone-functional support and methods of preparing such adduct supports.

The invention provides a chemically reactive support comprising a pre-existing support having surfaces and azlactone-functional moieties contacting the surfaces and modifying reactivity of such surfaces while retaining useful physical and chemical characteristics of the pre-existing support.

The invention also provides a method of preparing an azlactone-functional support, comprising the steps of (a) exposing surfaces of a pre-existing support with high energy radiation to generate free radical reaction sites on the surfaces and (b) causing azlactone-functional moieties to react with the free radical reaction sites to modify chemical reactivity of the pre-existing support.

The invention also provides a method of preparing an azlactone-functional support, comprising (a) covering surfaces of a pre-existing support with azlactone-functional monomers, crosslinking monomers, and optionally co-monomers, and (b) copolymerizing the monomers to form a crosslinked, polymerized, azlactone-functional moieties at surfaces of the pre-existing support to modify chemical reactivity of the pre-existing support.

The invention also provides an adduct support, comprising a chemically reactive support described above, having azlactone-functionality at surfaces of the support and a ligand comprising a nucleophilic reagent reacted with the azlactone-functionality.

A feature of the present invention is that methods of preparing the azlactone-functional modified surfaces do not compromise useful physical and chemical characteristics of the pre-existing support.

Another feature of the present invention is that azlactone-functional moieties are present only at surfaces of the pre-existing support, making efficient use of valuable azlactone-functionality.

Azlactone-functional modified surfaces of a pre-existing support are useful in surface-mediated or catalyzed reactions for synthesis or site-specific separations. Non-limiting examples of such uses include affinity separation of biomolecules from culture media, diagnostic supports, and enzyme membrane reactors. Azlactone-functional modified surfaces are capable of covalently binding azlactone-reactive, nucleophilic groups, such as Protein A, which is a biologically active material which reversibly binds to an antibody, such as Immunoglobulin G.

One method of the present invention involves the irradiation of surfaces of a pre-existing support with high-energy radiation to prepare free radical reaction sites on such surfaces upon which azlactone-functional moieties can be formed by homopolymerization, copolymerization, or grafted reaction with free radically reactive azlactone-functional moieties.

Another method of the present invention involves the polymerization or copolymerization of azlactone-functional moieties as crosslinked coatings on surfaces of pre-existing supports.

Another method of the present invention involves the the dispersion polymerization of azlactone-functional moieties to produce crosslinked azlactone-functional particles within the pores and interstices of a pre-existing porous support.

"Azlactone" means oxazolinone moieties of Formula I:

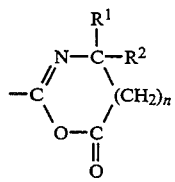

wherein $R^1$ and $R^2$ independently can be an alkyl group having 1 to 14 carbon atoms, a cycloalkyl group having 3 to 14 carbon atoms, an aryl group having 5 to 12 ring atoms, an arenyl group having 6 to 26 carbon atoms and 0 to 3 S, N, and nonperoxidic O heteroatoms, or $R^1$ and $R^2$ taken together with the carbon to which they are joined can form a carbocyclic ring containing 4 to 12 ring atoms, and n is an integer 0 or 1.

"Pre-existing support" means a matrix having surfaces not directly capable of forming covalent chemical bonds with nucleophilic reagents, especially biologically active materials.

"Surfaces" means both outer surfaces of a support and any applicable interior surfaces forming pores and interstices within a porous support.

"Biologically active material" means a chemical composition having nucleophilic-functional groups and capable of reacting in a manner which affects biological processes.

"High energy radiation" means radiation of a sufficient dosage and energy to cause the formation of free radical reaction sites on surfaces of supports. High energy radiation can include electron-beam radiation, gamma radiation, ultraviolet (uv) radiation, plasma radiation, and corona radiation.

It is an advantage of the present invention that only surfaces of a pre-existing support are chemically-modified, such that precious azlactone-functional moieties are not wasted within the bulk of a matrix of a support being formed in the presence of azlactone-functional materials.

It is another advantage of the present invention that surfaces of a pre-existing support are not physically and chemically modified in a manner which diminishes beyond usefulness the physical and chemical characteristics for which the pre-existing support was originally selected.

Thus, the present invention retains the benefits of the physical and chemical characteristics of the bulk properties of a pre-existing support while adding a chemical modification of azlactone-functionality to surfaces of a support which renders a pre-existing support useful in ways an unmodified support could not achieve.

In particular, the presence of azlactone-functionality allows for the covalent attachment, without intermediate chemical activation of the support, of nucleophilic-functional-group-containing materials, especially biologically active materials. Attachment of such materials, without intermediate chemical activation of the support, can provide utility as adsorbants, catalysts, reagents, complexing agents, or purification supports.

EMBODIMENTS OF THE INVENTION

Pre-existing Supports

Selection of a matrix to serve as a support can vary widely within the scope of the invention. A support can be porous or nonporous, depending on preferred final use. A support can be continuous or non-continuous depending on ultimate desired usage. A support can be made of a variety of materials, including supports made of ceramic, glassy, metallic, or polymeric materials or combinations of materials. A support can be flexible or inflexible depending on ultimate desired usage. Provision of azlactone-functionality on surfaces of such pre-existing supports does not adversely affect the bulk properties of the pre-existing support, other than providing azlactone-functionality which can react with various nucleophilic reagents without intermediate chemical activation.

Preferred matrices include polymeric supports, such as woven and nonwoven webs (such as fibrous webs), microporous fibers, and microporous membranes.

Webs

Woven and nonwoven webs are useful as supports having either regular or irregular physical configurations of surfaces from which azlactone-functional moieties can extend. Fibrous webs are particularly desired because such webs provide large surface areas, with nonwoven fibrous webs being preferred due to ease of manufacture, low material cost, and allowance for variation in fiber texture and fiber density. A wide variety of fiber diameters, e.g., 0.05 to 50 micrometers, can be used. Web thickness can be varied widely to fit the application, e.g., 0.2 micrometer to 100 cm thick or more.

Fibrous webs can be prepared by methods known in the art, or by modifications of methods known in the art. Nonwoven webs can be prepared by melt-blowing as is known to those skilled in the art and disclosed in, for example, U.S. Pat. No. 3,971,373, which is incorporated herein by reference. In general, a molten polymeric material is extruded in such a way as to produce a stream of melt blown polymer microfibers. The fibers are collected on a collection screen, with the microfibers forming a web.

The web optionally can be molded or pressed at a pressure of up to 90 psi to provide an article having a Gurley number of at least 2 seconds, as described in coassigned U.S. Pat. Nos. 5,328,758 and 5,415,779, incorporated by reference herein.

The nonwoven webs can also optionally include a permeable support fabric laminated to one or both sides of the web, as described in U.S. Pat. No. 4,433,024, or can additionally contain reinforcing fibers as described in U.S. Pat. Nos. 4,681,801 and 4,868,032, all of which patents are incorporated by reference herein.

The preferred materials useful to prepare nonwoven fibrous webs include polymers and copolymers of monomers which form fibrous webs. Suitable polymers include polyalkylenes such as polyethylene and polypropylene, polyvinyl chloride, polyamides such as the various nylons, polystyrenes, polyarylsulfones, poly(vinyl alcohol), polybutylene, poly(ethylene vinyl acetate), polyacrylates such as polymethyl methacrylate, polycarbonate, cellulosics such as cellulose acetate butyrate, polyesters such as poly(ethylene terephthalate), polyimides, and polyurethanes such as polyether polyurethanes, and combinations thereof.

Nonwoven webs can also be prepared from combinations of co-extruded polymers such as polyesters and polyalkylenes. Copolymers of the monomers which provide the above-described polymers are also included within the scope of the present invention.

Nonwoven webs can also be combined webs which are an intimate blend of fine fibers and crimped staple fibers.

Fibers and Membranes

Pre-existing, polymeric supports can also include microporous membranes, fibers, hollow fibers, or tubes, all of which are known in the art.

The same materials useful for preparing webs are also suitable for preparing fibers and membranes. Preferably, membranes are composed of homopolymers and copolymers of polyolefins. Nonlimiting examples of such polyolefins are polyethylene, polypropylene, polybutylene, and copolymers of ethylene and vinyl acetate.

A preferred technique useful for preparation of microporous thermoplastic polymeric supports is thermally induced phase separation which involves melt blending a thermoplastic polymer with immiscible liquid at a temperature sufficient to form a homogeneous mixture, forming an article from the solution into a desired shape, cooling the shaped article so as to induce phase separation of the liquid and the polymer and to ultimately solidify the polymer, and removing at least a substantial portion of the liquid leaving a microporous polymer matrix. This method and the preferred compositions used in the method are described in detail in U.S. Pat. Nos. 4,957,943; 4,539,256; and 4,726,989, which are incorporated herein by reference.

Alternatively, polymeric supports can also be hydrophobic polyolefin membranes prepared by thermally induced phase separation techniques, but also having a hydrophilic polymeric shell interlocked about such hydrophobic membrane surfaces. Coassigned U.S. patent application Ser. No. 08/122,807, the disclosure of which is incorporated by reference, discloses methods of preparation of such hydrophilized, microporous membranes using poly(vinyl alcohol) precursors to form an extremely thin poly(vinyl alcohol) shell about the polyolefin surfaces.

Alternatively, polymeric supports can be constructed from poly(vinyl alcohol), prepared using poly(vinyl alcohol) precursors, to form hydrogel materials, such as disclosed in U.S. Pat. Nos. 4,528,325 and 4,618,649, the disclosures of which are incorporated by reference herein. Alternatively, polymeric supports can be constructed from poly(methyl methacrylate) to form other hydrogel materials. Poly(methyl methacrylate) is commercially available and is often used in opthalmic devices such as intraocular lenses, contact lenses, and the like.

Alternatively, polymeric supports can also be prepared by solvent phase inversion polymerization techniques. Such techniques are disclosed in U.S. Pat. No. 5,006,247, the disclosure of which is incorporated by reference therein.

Other Supports

Ceramic supports, glass supports, and metallic supports are all known in the art and are commercially available or can be prepared by a variety of known techniques.

Azlactone-functional Moieties

Azlactone-functional moieties can be any monomer, prepolymer, oligomer, or polymer containing or comprising azlactone functionality of Formula I above and also comprising a site for free radical reaction. Preferably, such reaction site is a vinylic group on an unsaturated hydrocarbon to which azlactone of Formula I is attached. Such moieties can be individual azlactone-containing monomers, oligomers formed with free radical reaction sites and having azlactone-functionality derived from individual azlactone-containing monomers, or polymers having azlactone-functionality, derived from individual azlactone-containing monomers, and at least one free radical reacting site.

Azlactone-containing Monomers

Preferably, azlactone-functionality is provided by 2-alkenyl azlactone monomers. The 2-alkenyl azlactone monomers that can be grafted to or polymerized on surfaces of pre-existing supports are known compounds, their synthesis being described for example in U.S. Pat. Nos. 4,304,705; 5,081,197; and 5,091,489 (all Heilmann et al.) the disclosures of which are incorporated herein by reference.

Suitable 2-alkenyl azlactones include:
2-ethenyl-1,3-oxazolin-5-one,
2-ethenyl-4-methyl-1,3-oxazolin-5-one,
2-isopropenyl-1,3-oxazolin-5-one,
2-isopropenyl-4-methyl-1,3-oxazolin-5-one,
2-ethenyl-4,4-dimethyl-1,3-oxazolin-5-one,
2-isopropenyl-4,4-dimethyl-1,3-oxazolin-5-one,
2-ethenyl-4-methyl-4-ethyl-1,3-oxazolin-5-one,
2-isopropenyl-4-methyl-4-butyl-1,3-oxazolin-5-one,
2-ethenyl-4,4-dibutyl-1,3-oxazolin-5-one,
2-isopropenyl-4-methyl-4-dodecyl-1,3-oxazolin-5-one,
2-isopropenyl-4,4-diphenyl-1,3-oxazolin-5-one,
2-isopropenyl-4,4-pentamethylene-1,3-oxazolin-5-one,
2-isopropenyl-4,4-tetramethylene-1,3-oxazolin-5-one,
2-ethenyl-4,4-diethyl-1,3-oxazolin-5-one,
2-ethenyl-4-methyl-4-nonyl-1,3-oxazolin-5-one,
2-isopropenyl-4-methyl-4-phenyl-1,3-oxazolin-5-one,
2-isopropenyl-4-methyl-4-benzyl-1,3-oxazolin-5-one, and
2-ethenyl-4,4-pentamethylene-1,3-oxazolin-5-one, The preferred 2-alkenyl azlactones include 2-ethenyl-4,4-dimethyl-1,3-oxazolin-5-one (referred to herein as VDM) and 2-isopropenyl-4,4-dimethyl-1,3-oxazolin-5-one (referred to herein as IDM).

If a copolymer is to be formed, a co-monomer having similar or different chemical or physical properties can be included, depending on the desired characteristics for the graft or coating. Nonlimiting examples of co-monomers useful to be copolymerized with azlactone-functional moieties to form grafts or coatings include hydroxyethyl methacrylate (HEMA), vinyl acetate, or any of vinyl aromatic monomers; alpha, beta-unsaturated carboxylic acids or their derivatives or vinyl esters; vinyl alkyl ethers; olefins; N-vinyl compounds; vinyl ketones; or vinyl aldehydes. Nonlimiting examples of such co-monomers are disclosed in European Patent Publication 0 392 735, the disclosure of which is incorporated by reference.

Preferably, HEMA is used as a co-monomer in order to impart hydrophilicity to the azlactone-functional surface, in order to facilitate coupling of hydrophilic nucleophilic reagents to form adduct supports.

Such azlactone-functional monomers can be combined for copolymerizing with non-azlactone-functional monomers in any combination of weight percentages to control the reaction results.

For example, using a co-monomer of similar reactivity ratio to that of VDM will result in a random copolymer chain grafted to the free radical reaction site of the support.

Determination of reactivity ratios for copolymerization are disclosed in Odian, *Principles of Polymerization*, 2nd Ed., John Wiley & Sons, p. 425–430 (1981), the disclosure of which is incorporated by reference herein.

Alternatively, use of a co-monomer having a higher reactivity to that of VDM will result in a block copolymer chain grafted to the reaction site, with little or no azlactone-functional moieties near the reactive surface but considerable azlactone-functionality near the terminus of the chain. This construction places azlactone-functionality away from surfaces of the support (where steric hindrance might prevent the coupling of the azlactone-reactive nucleophilic reagent), but covalently bonded thereto for considerable reactivity with nucleophilic reagents.

Oligomers and Polymers

Although not as preferred as monomers, azlactone-functional prepolymers or oligomers and polymers or copolymers having at least one free-radically polymerizable site can also be utilized for providing azlactone-functionality on surfaces of a pre-existing support.

Azlactone-functional oligomers and polymers for example, are prepared by free radical polymerization of azlactone monomers, optionally with co-monomers as described in U.S. Pat. Nos. 4,378,411 and 4,695,608, incorporated by reference herein.

Polymers having azlactone-functional side chains can be prepared by reactive extrusion grafting of azlactone monomers to non-azlactone-containing polymers, using such techniques as disclosed in European Patent Publication 0 392 783 (Coleman et al.) incorporated by references herein.

Nonlimiting examples of azlactone-functional oligomers and prepolymers are disclosed in U.S. Pat. Nos. 4,485,236 and 5,081,197, and European Patent Publication 0 392 735, all incorporated by reference herein.

In order to be useful in the present invention, these azlactone-functional polymers and prepolymers must be modified so as to also comprise at least one free-radically polymerizable site. This is readily accomplished by reacting a portion of the azlactone-functional groups with an ethylenically unsaturated nucleophilic compound, such as those compounds disclosed in U.S. Pat. No. 4,378,411 identified above, thereby producing a polymer or prepolymer having both azlactone-functionality and free-radically reactive functionality. The ratio of azlactone moieties to unsaturated moieties can vary from 99:1 to 1:99, although it is preferable for the azlactone moiety content in the polymer or prepolymer to be at least fifty percent (50%).

Method of Providing Azlactone-Functional Surfaces on Pre-existing Supports

In general, processes for providing the azlactone-functional supports of the present invention involve exposing a pre-existing support, especially a pre-existing, polymeric support, to high energy radiation and to free-radically polymerizable azlactone-functional moieties. Exposure of a support to an azlactone-functional moiety can take place either simultaneously with or subsequent to the irradiation of the support. Depending on the the type of radiation and other process conditions, the azlactone-functional polymer which is produced can be either grafted to the surface of the pre-existing support or can be formed as a coating on the support or can become particles enmeshed within void spaces of the support. In the former instance, the azlactone-functional moiety becomes covalently linked to the support, whereas in the latter two instances, it does not. Regardless, the pre-existing support is transformed into being capable of forming chemical bonds with nucleophilic reagents, especially biologically active materials.

Methods of Irradiation

Pre-existing supports are subjected to radiation from a high-energy source to form free radical sites on or near surfaces of such supports. In the case of nonpolymeric supports, no free radical sites are formed on surfaces. However, during plasma or corona treatment, free radical sites are formed from the monomer molecules adsorbed onto the nonpolymeric support surfaces. High energy radiation can be classified for the purposes of the present invention as either penetrating or non-penetrating. Penetrating radiation is utilized when one wants to provide azlactone-functionality to both the interior and exterior surfaces of a pre-existing support, whereas non-penetrating radiation is useful to provide azlactone-functionality only to the outer surfaces of the pre-existing support.

Nonlimiting examples of penetrating radiation include beta, gamma, electron-beam, x-ray, uv and other electromagnetic radiation, whereas non-penetrating radiation includes alpha, plasma, and corona radiation. In some instances, corona radiation can be become penetrating irradiation.

Penetrating Irradiation

Many forms of penetrating radiation are of sufficiently high energy, that when absorbed by a pre-existing support, sufficient energy is transferred to that support to result in the cleavage of chemical bonds in that support. Homolytic chemical bond cleavage results in the formation of a free radical site on the support. Thus, this type of radiation is useful when it is desired to covalently link the azlactone-functional moieties, via a free radical grafting reaction, to the surfaces of a pre-existing support. Electron beam and gamma radiation are preferred for this method of grafting due to the ready-availability of commercial sources.

It should be noted that, although penetrating radiation also generates free radical sites within the bulk of many supports, these sites are generally not as available for reactions with azlactone-containing moieties because such moieties are less likely to diffuse into the bulk of a support than react at an outer surface of that support. Thus, even with penetrating radiation to generate reaction sites, azlactone-functionality is usually found principally at outer surfaces of a support.

Sources of electron-beam radiation are commercially available, including an Energy Sciences Inc. Model CB-150 Electrocurtain Electron Beam Processor. Sources of uv radiation are high and medium pressure mercury lamps, deuterium lamps, and "blacklights" emitting 180 nm to 400 nm (with preferred maximum intensity at about 360 nm) light, which are commercially available from a number of vendors, including General Electric Company and GTE Sylvania. Sources of gamma irradiation are commercially available from Atomic Energy of Canada, Inc. using a cobalt-60 high-energy source.

High energy radiation dosages are measured in megarads (Mrad) or kilograys (kGy), which is 1/10 of a mRad. Doses can be administered in a single dose of the desired level or in multiple doses which accumulate to the desired level. Dosages can range cumulatively from about 10 kGys to about 200 kGys and preferably from about 30 kGys to about 100 kGys. Preferably, the cumulative dosage exceeds 30 kGys (3 Mrads).

Supports can be irradiated in a package or container where the temperature, atmosphere, and other reaction parameters can be controlled.

Temperature can be ambient temperature.

The atmosphere can be air or preferably an inert atmosphere such as nitrogen.

The pressure in the container can be atmospheric, elevated or depressed to a partial or complete vacuum. Preferably it is atmospheric.

Depending upon the control of the irradiation conditions, supports can be irradiated in a batch or continuous process.

After irradiation and prior to contact with the azlactone-functional moiety, the atmosphere around the surfaces should be kept free of free-radically reactive substances, especially $O_2$.

After the first step where irradiation forms free radical reaction sites, the second step provides azlactone-functional moieties to react with such sites under suitable free radical reaction conditions.

Generally, irradiation can take place in the presence or absence of the azlactone-functional moieties. When conducted in the presence of azlactone-functional moieties, ungrafted free-radical (co)polymerization can occur in addition to grafting polymerization. As a consequence, it can be preferred to irradiate a pre-existing support in the absence of azlactone-functional moieties followed by contacting the irradiated support with azlactone-functional moieties to initiate the desired free radical grafting reaction. This may be accomplished by immersing the support in, coating the support with, or spraying the support with vapors, dispersions, or solutions containing azlactone-functional moieties. Alternatively, production of water-soluble azlactone-functional polymers can be minimized during irradiation in the presence of azlactone-functional moieties by incorporation of a multifunctional cross-linking monomer.

Another method of radiation-induced grafting involves irradiation of a polymer film with ionizing radiation in the presence of ambient oxygen to generate hydroperoxide functionality on the surface. The peroxides are then used to initiate graft-polymerization of olefinic monomers by thermally induced free radical polymerization, according to techniques disclosed in Gupta et al., *Eur. Polym. J.,* 25 (11), 1137 et seq. (1989). Alternatively, hydroperoxide species can be used to initiate graft polymerization, according to techniques disclosed in Yamauchi et al., *J. Appl. Polym. Sci.,* 43, 1197 et seq. (1991).

Ultraviolet radiation, which is a penetrating radiation for purposes of the present invention, is different from other penetrating radiations in that uv radiation does not provide enough energy directly to most supports to produce free radical sites. Therefore, uv radiation is generally conducted in the presence of both azlactone-functional moieties and photoinitiators, which absorb light in the uv-visible range (250–450 nm) and convert this light energy to chemical energy in the form of free radical species. Generation of free radicals by photoinitiators generally occurs by one of two processes, intramolecular bond cleavage or intermolecular hydrogen abstraction. Suitable photoinitiators are identified in Oster et al., "Photopolymerization of Vinyl Monomers" *Chem Rev.,* 68, 125 (1968), the disclosure of which is incorporated by reference. Nonlimiting examples include acyloins and derivatives thereof; diketones; organic sulfides; S-acyl dithiocarbamates; phenones; sulfonyl halides; and azo compounds. Of these possible photoinitiators, azobis(isobutyronitrile), acyloins, acyloin ethers, and benzil ketals and 1-phenyl-2-hydroxy-2-methyl-1-propanone (commercially available as Darocure TM 1173 brand photoinitiator from E Merck) are preferred.

The manner in which the azlactone-functional surface is imparted to the pre-existing support can be influenced by the choice of photoinitiator. Whereas most photoinitiators will promote free radical (co)polymerization of azlactone-functional moieties to produce coatings, those initiators which are prone to abstraction reactions, particularly phenones, result in simultaneous grafting to the pre-existing support. It is preferred to utilize crosslinking comonomers with uv irradiation to minimize the production of soluble polymer.

A support can be immersed in, sprayed with, dipped into, or otherwise contacted with a mixture, dispersion or solution of azlactone-containing monomers, photoinitiator, and optionally a crosslinking monomer and/or non-azlactone-containing co-monomer(s). Then, the coated support is exposed to uv radiation to cure the monomers, thus resulting in the formation of azlactone-functional copolymer as a continuous or discontinuous coating on surfaces of the support.

After rinsing to remove unreacted monomers and drying, an azlactone-functional support is available for nucleophilic reaction.

Nonlimiting examples of crosslinking monomers for these azlactone-functional coatings include ethylene glycol dimethylacrylate (EGDMA), trimethylolpropane trimethacrylate (TMPTMA), methylenebisacrylamide (MBA), and divinylbenzene.

Nonlimiting examples of co-monomers include hydroxyethyl methacrylate (HEMA), butyl acrylate (BA), isooctyl acrylate (IOA), butyl methacrylate (BMA), and isobutyl methacrylate (IBMA).

In some instances, the azlactone-functional copolymer is deposited as small particles or aggregates of small particles contacting the surfaces or otherwise within the porous structure of the pre-existing support.

Coating and uv photopolymerization can occur in ambient conditions.

Temperature can be about $-78°$ C.–$100°$ C. and preferably is ambient.

Atmospheric conditions need to be inert using non-oxygen gases and preferably is nitrogen or a noble gas such as argon. Alternatively, a web coated with the desired monomer solution can be placed between two oxygen-occluding sheets that are transparent to the desired type of radiation.

Since free radical reactions occur quickly, the contact time of the irradiated support with the azlactone-functional moiety ranges from momentary to less than 30 min., depending on radiation intensity. Reaction times as short as a few seconds are often enough to provide completed reaction.

Non-Penetrating Irradiation

Plasma and corona radiation differ from penetrating irradiation techniques because only the outer surfaces of a pre-existing support are subjected to treatment with vaporous, excited azlactone-functional moieties. This method of irradiation grafting only requires one step.

Electrical energy in the form of plasma discharge (also known as glow discharge) or corona discharge activates the azlactone-functional moieties in the vapor state for contact with the outermost surfaces of the support. The outermost surfaces can include adsorbed monomer molecules. Without being bound to a particular theory, it is believed that the excited azlactone-functional moieties react with surface free radical sites leading to the deposition of a thin film or network coating the support.

Even though ethylenically unsaturated monomers are not required for non-penetrating radiation methods, preferably, suitable azlactone-functional moieties are monomeric and covalently react with free radical sites on the supports.

As with penetrating irradiation techniques, one can control the nature of the azlactone-functionality formed by employing various amounts of azlactone-functional moieties and non-azlactone-functional moieties and by introducing such amounts into the reaction vessel at different times.

For example, one can form a corona-treated support having a crosslinked coating or network of VDM and HEMA covalently bound thereto. Alternatively, one can form a plasma-treated support having layers of deposited HEMA and VDM extending from the support. Alternatively, one can treat regiospecific surfaces of a pre-existing support. By preventing certain portions of surfaces from being subjected to corona or plasma discharge treatment, one can produce supports having specific regions of azlactone-functionality.

Alternatively, one can treat regiospecific surfaces sequentially with different azlactone-functional moieties to produce a complex surface of a support for multiple or differentiating nucleophilic reactions.

Sources of plasma discharge energy operate typically at DC, AC, high, radio, or microwave frequencies. Such sources are commercially available from a number of vendors including ENI Power Systems, Inc. The excitation frequency is typically 0–2.5 GHz, preferably 25–125 kHz. The power density at the support's surface is typically $1 \times 10^{-3}$–0.4 W/cm$^2$ where the normalization is based on the projected area of the support (as opposed to its actual surface area, if porous). Preferably, the power density is 0.01–0.05 W/cm$^2$. The gas/vapor composition comprises azlactone-functional moieties, either pure or mixed with other organic or inorganic vapors or gases. Nonlimiting examples of such vapors or gases include He, Ar, NO$_2$, CO, and CO$_2$; alkanes, alkenes, alkynes; functionalized alkanes, alkenes, and alkynes; acrylates, methacrylates; and other comonomer candidates identified above with respect to copolymerization of azlactone-functional moieties.

Sources of corona discharge energy are available commercially from a number of vendors, including ENI Power Systems, Inc. The excitation frequency is typically 5–100 kHz, preferably 10–50 kHz.

The pressure is typically 0.5–5 atmospheres, preferably at or near 1 atmosphere.

The power density is typically 0.5–6 W/cm$^2$, preferably 1–3 W/cm$^2$, when applying the same normalization of surface area as described with respect to plasma discharge above.

The amount of deposition of azlactone-functional moieties can be controlled by the amount of time exposed to discharge. The amount of time using the above power densities can range from 0.05 secs to several hours, and preferably from about 1 second to about 5 minutes.

The gas/vapor composition comprises azlactone-functional moieties mixed with other organic or inorganic gases or vapors, from among the candidates described above with respect to plasma discharge. Preferably, the azlactone-functional moieties have a partial pressure of 1–100 mTorr.

It has recently been published in European Patent Publication 0 467 639 (1991) that a process believed to involve corona discharge can effectively achieve penetrating irradiation effect on nonwoven material using a Helium atmosphere and dielectric protection over both electrodes of the corona discharge apparatus. With this technique, one can employ corona discharge of azlactone-functional moieties to render interior surfaces of a porous support azlactone-functional. Power densities and time of discharge described above for non-penetrating irradiation need not change.

Adduct Supports and Usefulness of the Invention

Because azlactone-functional moieties occupying a surface of a pre-existing support are capable of multiple chemical reactions, azlactone-functional modified surfaces of the present invention can form adduct supports.

Once covalently bonded to or otherwise coating a surface, electrophilic azlactone-functional moieties can react through a nucleophilic ring opening reaction at the carbonyl group with any of a myriad of nucleophilic reagents. The result is the formation of an adduct support having specific reactivities determined by the nature of the nucleophilic reagent employed in the reaction.

Nonlimiting examples of nucleophilic reagents include biologically active materials, acids, bases, chelators, hydrophiles, lipophiles, hydrophobes, zwitterions, detergents, and any other chemical which can react with the azlactone-functionality to confer on the surfaces of the pre-existing support a modified reactivity which differs from that which existed on the support prior to azlactone-functionality modification. For example, one can modify a hydrophobic surface by reacting on azlactone-functional adduct support with a nucleophilic, hydrophilic moiety. Examples of nucleophilic, hydrophilic compounds include poly(ethylene oxide) commercially available as Jeffamines from Texaco, Inc.

Thus, surfaces of a support can become azlactone-functional and then adduct-reactive, without loss of the physical and chemical characteristics of such supports such as porosity, flux, color, surface area, permeability, solvent resistance, hydrophilicity, flexibility, mechanical integrity, and other stability or feature in the use environment. Unexpectedly, pre-existing supports can add all of the benefits of azlactone-functionality without an effective diminution of the physical and chemical characteristics of bulk properties of the pre-existing support.

Ligands and Adduct Supports

Adduct supports have ligands coupled or otherwise tightly bound to azlactone-functional moieties extending from surfaces of supports to form biologically or chemically active reaction sites. For direct coupling, nonlimiting examples of nucleophilic ligands include primary and secondary amines, alcohols, and mercaptans. Of these, amine-functional ligands are especially preferred.

While not being limited to a particular theory, it is believed that a ligand forms a covalent bond when coupled to an azlactone-functional moiety.

Ligands useful for the preparation of adduct supports can also vary widely within the scope of the present invention. Preferably, a ligand is chosen based upon the contemplated end use of the adduct support.

Once ligands are coupled to azlactone-functional grafts or coatings, such ligands are available for biological or chemical interaction, such as adsorbing, complexing, catalysis, or reagent end use.

Adduct supports are useful as adsorbants, complexing agents, catalysts, reagents, as enzyme and other protein-bearing supports, and as chromatographic articles.

In a preferred aspect of the present invention, the ligand desired for coupling is a biologically active material having azlactone-reactive, nucleophilic-functional groups. Nonlimiting examples of biologically active materials are substances which are biologically, immunochemically, physiologically, or pharmaceutically active. Examples of biologically active materials include proteins, peptides, polypeptides, antibodies, antigenic substances, enzymes, cofactors, inhibitors, lectins, hormones, receptors, coagulation factors, amino acids, histones, vitamins, drugs, cell surface markers, and substances which interact with them.

Of the biologically active materials, proteins, enzymes and antigenic substances are desired for coupling to azlactone-functional supports. Nonlimiting examples of proteins, enzymes, and antigenic substances include natural and recombinant Protein A (ProtA), Immunoglobulins such as rat (rIgG), human (hIgG), bovine (bIgG), rabbit (rbIgG), and mouse (mIgG), Concanavalin A (ConA), Bovine Serum Albumin (BSA), Thyroglobulin (TG), Apoferritin (Af), Lysozyme (Ly), Carbonic Anhydrase (CA), Lipase, Pig Liver Esterase, Penicillin acylase, and Bacterial Antigen (BA). Uses for immobilized proteins, enzymes and antigenic substances are disclosed in European Patent Publication 0 392 735.

A presently preferred biologically active material is ProtA because of its multitude of uses in bioseparations.

Alternatively, an adduct support of the present invention can comprise a coupled enzyme to catalyze a chemical transformation of substances recognized by the enzyme. Also, a support comprising a coupled antigenic substance can be utilized for affinity purification of a corresponding antibody from a complex biological fluid flowing through the porous matrix of the adduct support. In other examples, an adduct support having Protein A coupled to internal and external surfaces can adsorb biologically active materials such as Immunoglobulin G for affinity separations processes. In other examples, an adduct support can be used for immobilization of antibodies or be used for immunodiagnostics or for Western blotting.

Alternatively, the ligand can be a hydrophile for improving compatibility of mammalian body implants, such as intraocular lenses, with adjoining tissues. One example of a ligand especially suitable for chemically modifying body implants is an anticoagulant, such as a chemically-modified heparin, e.g., an amine-terminated heparin.

Azlactone-functional moieties will undergo nucleophilic attack by amines, thiols, and alcohols. Thus, ligands having at least one amine, thiol, or alcohol group thereon are candidates for coupling to azlactone-functional surfaces. Amine-functional ligands are preferred due to ease of reaction and stability of the linkage so formed.

Coupling of ligands to preferred azlactone-functional surfaces can use methods of using inorganic or organic polyanionic salts in such concentrations as to achieve high broad specific biological activity for the coupled ligand, such as methods disclosed in coassigned U.S. Pat. No. 5,200,471, the disclosure of which is incorporated by reference.

Coupling of ligands to preferred azlactone-functional surfaces according to the present invention results in adduct supports having the formula

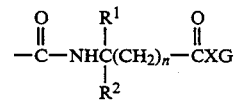

wherein
$R^1$, $R^2$ and n are as previously defined, $R^3$ is H or $CH_3$,
X can be $-O-$, $-S-$, $-NH-$, or $-NR^4$ wherein $R^4$ can be alkyl or aryl, and
G is the residue of HXG which performs the adsorbing, complexing, catalyzing, separating, or reagent function of the adduct support.

HXG is a nucleophilic reagent and can be a biologically active material, dye, catalyst, reagent, and the like.

Ligands having azlactone-reactive, amine, hydroxy, or thiol nucleophilic functional groups react, either in the presence or absence of suitable catalysts, with azlactone-functional groups by nucleophilic addition as depicted in the equation.

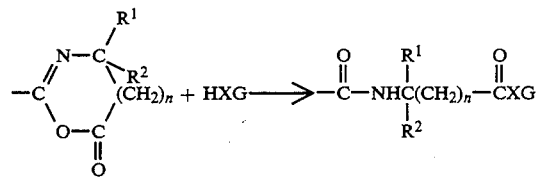

wherein
$R^1$, $R^2$, $R^3$, n, X, and G are as previously defined.

Depending on the functional group present in the ligand, catalysts may be required to achieve effective attaching reaction rates. Primary amine functional groups require no catalysts. Acid catalysts such as trifluoroacetic acid, ethanesulfonic acid, toluenesulfonic acid, and the like are effective with hydroxy and secondary amine functional groups.

In other aspects of the invention, the ligand is not biologically active but has other properties which lead to its end use. For example, the ligand can contain ionic functional groups. In that event, the resultant adduct article may be utilized in ion exchange type applications. Suitable ionic groups include carboxylic acid, sulfonic acid, phosphonic acid, tertiary amine, and quaternary amine groups. Examples of useful ionic group containing ligands include aminocarboxylic, sulfonic, or phosphonic acids such as glycine, alanine, leucine, valine, β-alanine, γ-aminobutyric acid, 1- and 3-aminopropyl-phosphonic acid, taurine, γ-amino octanoic acid, aminomethylphosphonic acid, amino-methanesulfonic acid, and the like; hydroxy-acids such as isethionic acid, 3-hydroxy-propane sulfonic acid, lactic acid, glycolic acid, hydroxymethylphosphonic acid, p-hydroxybenzoic acid, and the like; and amino- and hydroxy-functional tertiary and quarternary amines such as 2-diethylaminoethylamine, 3-dimethyl-aminopropylamine, N,N-diethylethanol-amine, and the like, and quaternized versions thereof. When the amine-, hydroxy- or thiol-functional ligand is a simple aliphatic and/or aromatic hydrocarbon, the resultant adduct article may be useful in reverse phase or hydrophobic interaction type chromatographic processes. Reaction of the support of this invention with very hydrophilic or hydrophobic ligands can be used to produce adduct articles displaying highly absorbant properties towards aqueous or oily fluids, respectively. Other types of ligands and uses will be obvious to one skilled in the art and are considered to be within the scope of the present invention.

Objects and advantages of this invention are further illustrated by the following examples, but the particular materials and amounts thereof recited in these examples, as well as other conditions and details, should not be construed to unduly limit this invention.

EXAMPLES

Example 1

Preirradiation Electron Beam Grafting of Hydrophobic Polyethylene (PE) Microporous Membrane with 2-Vinyl 4,4-dimethylazlactone (VDM)

A PE microporous membrane, prepared according to the method of Example 23 of U.S. Pat. No. 4,539,256 (Shipman), incorporated by reference herein, having a pore size of 0.496 μm, a thickness of 73.9 μm and a void volume of 81.5%, was passed through an electron beam (e-beam) chamber within a Model 1 Electrocurtain CB-300/30/380 (manufactured by Energy Sciences, Inc., Wilmington, Mass.) to generate free radicals on the membrane. The accelerating voltage of the e-beam was 150 KV, with total irradiation dose of 50 kGys (5 Mrads). Membrane samples (7.6×12.7 cm) were passed through the e-beam equipment taped to a polyester carrier web traveling at 6.1 m/min.

The samples exited the e-beam chamber directly into a $N_2$ purged box, where they were removed from the carrier and immersed into a solution of VDM (SNPE, Princeton, N.J.) dissolved in ethyl acetate. The inert atmosphere in the glove box was intended to prevent premature quenching of the generated radicals by oxygen. The monomer solutions had concentrations of 25, 50, and 100 volume-percent VDM and had been purged with argon for 1 h to displace any dissolved oxygen. Irradiated membranes were soaked in the monomer solution for 3 to 5 min. followed by a 5 min. soak in pure ethyl acetate to wash out excess monomer. They were dried and placed in zip-lock bags to prevent possible hydrolysis of the azlactone by atmospheric moisture.

Fourier-transform infrared spectroscopy (FT-IR) was used to characterize the grafted membranes. The ratio of the azlactone carbonyl absorption (1824 cm−1) to the PE C-H band (1462 cm−1) gives a relative measure of the bound azlactone. Ratios of 0.023, 1.78, and 1.27 were found for the samples reacted with 25, 50, and 100% VDM, respectively.

To confirm that all of the VDM was indeed covalently grafted to the membrane, the samples were extracted by three 15 min. soakings in pure ethyl acetate (three replicates of each). Weight loss values were 1.1, 0.7, and 0.0%. Since there was a weight gain of at least 10% during the grafting step, it was concluded that 90% or more of the VDM was covalently bonded.

COMPARISON EXAMPLE 2

Mutual Irradiation E-Beam Grafting onto PE Microporous Membranes

As a demonstration of the advantage of preirradiation grafting over that of mutual irradiation, the same microporous PE membrane as used in Example 1 was saturated with 10% (w/v) VDM/ethyl acetate solution just prior to being passed through the e-beam chamber for exposure at a dose of about 50 kGy. The membrane was rinsed in pure ethyl acetate for about 5 min. upon emergence from the e-beam chamber to remove unpolymerized monomer. The azlactone:PE ratio by FT-IR was 1.39, indicating that a substantial amount of the VDM was indeed bound to the membrane. The membrane weight decreased by 10% following the extended solvent soaking procedure described in Example 1, indicating that a significant portion of the VDM was not grafted to the membrane. It is also likely that homopolymers of VDM (not bound to the membrane) accounted for much of the VDM which was not readily washed from the membrane because of entrapment within the membrane.

EXAMPLE 3

Preirradiation E-beam Grafting of Hydrophilized PE Microporous Membranes

The starting PE microporous membrane from Example 1 was hydrophilized by coating the internal and external pore surfaces with a 4% (w/v) solution of poly(vinyl trifluoroacetate) (PVTFA) followed by reaction with ammonia gas to convert the PVTFA to a highly crystalline poly(vinyl alcohol), a hydrophilic polymer, using the procedures described in Example 7 of coassigned, copending U.S. patent application Ser. No. 08/122,709 (Gagnon et al.) published as PCT Publication WO 92/07899). Grafting conditions were the same as described in Example 1 except for the addition of 30 kGy and 100 kGy treatments. The FT-IR results are given in Table 1.

TABLE 1

The Effect of Varying the Irradiation Dose and Azlactone Concentration on the Ratio of the Azlactone-to-PE IR Signals
FT-IR Ratio (1824:1462 cm-1) at Various Irradiation Doses (kGys)

| VDM % | Dose (kGys) | | |
|---|---|---|---|
| | 30 | 50 | 100 |
| 25 | — | 0.38 | — |
| 50 | 1.70 | 1.32 | 5.06 |
| 100 | 1.10 | 5.23 | 0.96* |

The marked (*) membrane was completely filled with polymer and swelled upon solvent rinse. Upon drying it was too thick for accurate IR measurement; thus the ratio is not indicative of the amount of grafted VDM.

A surface area measurement was performed according to the following method: A sample measuring approximately 3 cm×5 cm was placed in a tared sample holder of a Quantasorb BET Surface Area Analyzer (Quantachrome Corp.). The sample was degassed by flushing with helium at 50° C. for 1 hr. The sample holder was then immersed in liquid nitrogen, and a helium/Krypton gas mixture was passed through the sample. At this temperature, only the Krypton will adsorb onto the surfaces of the sample, thus depleting the Krypton in the gas mixture passed through the sample. The surface area calculation is based upon the assumption that the probe gas adsorbs on all available sample surface area in a monolayer; thus the amount adsorbed times the adsorbate cross-sectional area is proportional to the specific surface area. The depletion of Krypton from the mixture, (i.e., the amount of Krypton adsorbed) is detected with a sensitive thermal conductivity detector. Upon rewarming of the sample to room temperature, the adsorbed Krypton is released and also quantified. The amount of adsorbed Kryton and the mass of the sample are used to calculate the specific surface area/unit mass value.

The above BET surface area measurement was performed on the unirradiated hydrophilic membrane control and on the 50 kGy-100% sample showed that the control value (18.6 m$^2$/g) had been reduced by over 50% to 8.1 m$^2$/g by the grafting of poly(vinylazlactone), which is not deemed to be diminished beyond usefulness of the membrane.

In all instances but one (30 kGy/50%), there was no detectable weight loss following the extended solvent extraction described in Example 1. Of the possibilities, the process employing 50 kGy/25% seemed to be the best compromise to avoid pore blockage while providing azlactone functionality.

EXAMPLE 4

Reaction of Azlactone-Grafted Hydrophilic PE Membrane with Ammonia

Portions of the treated membranes described in Examples 1 and 3, each prepared using 50 kGy and 50% VDM, were placed in an ammonia atmosphere in an enclosed glass vessel by suspending them above a concentrated NH$_4$OH solution for 10 min. at ambient temperature. FT-IR (using a Model FTS-40 spectrophotometer, Bio-Rad, Digilab Div., Cambridge, Mass.) measurements of both ammonia-reacted membranes and unreacted control membrane showed that the 1824 cm−1 azlactone absorbance band on the ammonia-reacted membranes had nearly entirely disappeared and that a new band appeared at 1659 cm−1 which is indicative of an amide bond. This confirmed that virtually all of the azlactone is available for reaction. These results show that almost any type of surface chemistry might be prepared from an azlactone-grafted membrane surface by choosing as a secondary reagent one which has both the desired functionality and an amine functionality.

EXAMPLE 5

E-beam-Grafting of Azlactone to Porous Polyethylene Films Increases the Amount of Coupled Protein Azlactone-functional and ungrafted control membranes were prepared as described in Example 3. Protein solutions were radiolabeled using Iodo-Beads TM beads (commercially available from Pierce Chem., Rockford, Ill.) and NaI-125 (Dupont NEN, Billerica, Mass.) using the procedures described in the product insert. Specific radioactivities obtained were: Protein A, (Genzyme, Boston) 2782 cpm/µg; immunoglobulin G (IgG, Sigma Chem., St. Louis), 2000 cpm/µg; and bovine serum albumin (BSA, Sigma), 2885 cpm/µg.

Circular portions (7 mm diameter) of the membrane were cut out using a paper punch. The membrane discs were then incubated with radiolabeled protein in 250 µl of 25 mM sodium phosphate, 150 mM NaCl, pH 7.5, for 60 min. at ambient temperature. Some membranes were reacted with 3.0M ethanolamine, pH 9.0, for 30 min. prior to the protein incubation to "deactivate" the azlactone functionality. Following the protein incubations all membranes were reacted an additional 15 min. with 500 µl of the ethanolamine reagent to inactivate remaining azlactones as well as rinse out unbound protein. Each membrane was subsequently rinsed an additional three times with 500 µl of the phosphate buffer. After the bound radioactivity was determined using a Model 5230 Auto-Gamma scintillation counter (Packard, Downers Grove, Ill.), the membranes were incubated for 4 h at 37° C. in 500 µl of 1.0% sodium dodecylsulfate (SDS) solution followed by determination of residual radioactivity. SDS is a strongly denaturing detergent capable of removing all but the most tenaciously bound protein. In these experiments, control membranes were completely untreated. These and all experiments described in this example were performed in triplicate.

TABLE 2

The Binding of Three Proteins to E-beam-Grafted and Control Porous Membranes

| Membrane | Total Bound Protein (µg/cm$^2$) | SDS Resistance(%) | Coupled Protein (µg/cm$^2$) |
|---|---|---|---|
| With Protein A | | | |
| Untreated | 4.0 | 14 | 0.55 |
| Untreated Quenched | 4.2 | 11 | 0.50 |
| Grafted | 3.2 | 58 | 1.86 |
| Grafted Quenched | 2.7 | 21 | 0.57 |
| With Immunoglobulin G | | | |
| Untreated | 7.2 | 18 | 1.24 |
| Untreated Quenched | 8.9 | 11 | 0.95 |
| Grafted | 6.1 | 45 | 2.74 |
| Grafted Quenched | 4.8 | 27 | 1.31 |
| With Bovine Serum Albumin | | | |
| Untreated | 3.4 | 18 | 0.59 |
| Untreated Quenched | 3.6 | 15 | 0.53 |
| Grafted | 1.7 | 68 | 1.18 |
| Grafted Quenched | 1.4 | 31 | 0.42 |

Consistently for all three proteins there was at least a two-fold increase in the amount of coupled protein as a result of the e-beam/VDM treatment. This was especially surprising because there is a decrease in total binding. The cause of the decrease in total binding was uncertain since this series included no e-beam only or e-beam plus solvent controls; however, it was presumed that the 50% reduction in total surface area (compare with Example 3) is the reason.

Treatment of the membrane with ethanolamine to inactivate the azlactone functionality reduced the amount of coupled protein to about the level of untreated membranes.

EXAMPLE 6

The Binding of Radiolabeled Protein to E-Beam Grafted Porous Polyethylene Membrane Unless indicated otherwise, all grafting procedures are identical to the 50 kGy example described in Example 3. Membranes were treated as described in Example 5. Protein A specific radioactivity was 1884 cpm/$\mu$g. Membranes were incubated overnight (16 h) with continuous rocking and treatment with ethanolamine was increased to 60 min. Controls were e-beam-treated only and e-beam-treated plus solvent-treated.

TABLE 3

Binding Protein A to E-beam Grafted and Control Porous Membranes

| Membrane | Total Bound Protein ($\mu$g/cm$^2$) | SDS Resistance(%) | Coupled Protein ($\mu$g/cm$^2$) |
| --- | --- | --- | --- |
| E-beam | 9.1 | 33 | 3.0 |
| E-beam + Solvent | 7.9 | 25 | 2.0 |
| E-beam + 50% VDM | 7.0 | 56 | 3.9 |
| E-beam + 100% VDM | 7.4 | 85 | 6.4 |

The solvent treatment caused a 13% decrease in the amount of protein which bound to an e-beam-treated membrane, because of the solvent solubilizing some of the hydrophilizing shell of poly(vinyl alcohol) which is required for the membrane to wet. There was no significant effect of azlactone on the total binding (which is probably proportional to the total available surface area); however, there was a pronounced effect of azlactone on the quality of the protein binding, i.e., a large increase in the amount of the protein which is so tightly bound, i.e., coupled, that it resists removal by SDS. Although it is not precisely accurate to ascribe covalency to the SDS resistant fraction, it is highly probable that increases in SDS resistance reflect increases in covalent binding.

Also, increasing the incubation time for the protein binding step from 1 h (Example 5) to 16 h increased the amount of the total binding 2.5-fold and the amount of coupling 3.5-fold. Thus, a 1 h incubation did not allow for full, but passive diffusion of the protein through the membrane.

EXAMPLE 7

The Effect of VDM Concentration on Protein Binding

Membranes were irradiated with 50 kGy and treated as described in Example 3 and protein coating procedures were identical to those in Example 6. Protein A specific radioactivity was 1767 cpm/$\mu$g.

TABLE 4

Effect of VDM Concentration on Protein Binding

| Membrane | Total Bound Protein ($\mu$g/cm$^2$) | SDS Resist. (%) | Coupled Protein ($\mu$g/cm$^2$) | IR Ratio* |
| --- | --- | --- | --- | --- |
| E-beam | 7.53 | 25% | 1.84 | 0.0 |
| E-beam + solvent | 6.97 | 21 | 1.47 | 0.0 |
| E-beam + 25% VDM | 6.55 | 30 | 1.97 | 0.168 |
| E-beam + 50% VDM | 6.19 | 36 | 2.20 | 0.638 |
| E-beam + 100% VDM | 2.58 | 67 | 1.73 | 0.540 |

*Ratio of the absorbance of 1824 cm-1 azlactone band to 1462 cm-1 polyethylene band.

There were two effects of increasing VDM concentrations: 1) A concentration-dependent increase in the percent of SDS resistant protein; 2) a concentration-dependent decrease in the total protein binding. These effects combine to yield an optimum amount of coupled Protein A at 50% VDM. These opposing effects were consistent with reduced access of protein caused by exceedingly long chains of poly(VDM) at high VDM concentrations, blocking protein access to the inner membrane surfaces.

EXAMPLE 8

Retention of Biological Activity of Membrane-Bound Protein

It was found that Protein A bound covalently to the porous PE membrane through azlactone retained its ability to bind human IgG. This was accomplished by a two-part experiment: determination of Protein A binding using radiolabeled Protein A, and, in parallel, determination of the amount of radiolabeled IgG bound to membrane-bound unlabeled Protein A.

Membranes were prepared as described in Example 3. All binding procedures were identical to Example 5 except that incubations with Protein A (whether radiolabeled or not) were for 5.5 h. Radioactivity determinations were made on those membranes which had been incubated with radiolabeled Protein A (1590 cpm/$\mu$l specific radioactivity). Those membranes which had been bound with unlabeled Protein A were incubated an additional 16 h with radiolabeled IgG (specific radioactivity: 1500 cpm/$\mu$g). They were rinsed, and IgG binding was determined by isotopic decay followed by the SDS step and a repeat of the binding determination. The results from this series of experiments are found in Table 5. The control membranes were e-beam- and solvent-treated.

TABLE 5

The Binding of IgG to Protein A-Coupled Membrane

| Membrane | Protein A | | Immunoglobulin G | |
| --- | --- | --- | --- | --- |
| | Total Protein A Bound ($\mu$g/cm$^2$) | SDS Resist. (%) | Total IgG Bound ($\mu$g/cm$^2$) | SDS Resist. (%) |
| Control | 7.66 | 20 | 12.1 | 2.9 |
| Control + 25% VDM | 6.84 | 31 | 10.6 | 3.4 |
| Control + 50% VDM | 5.63 | 42 | 9.9 | 3.5 |
| Control + 100% VDM | 3.03 | 57 | 3.8 | 4.4 |

The higher SDS resistances for the coupling of Protein A to the grafted membrane (compared to the binding of IgG to the Protein A-derivatized, grafted membrane) showed that Protein A was bound covalently to the membrane and IgG was bound non-covalently to the Protein A. The SDS resistances of 3–4% indicate that the VDM was almost completely inactivated. As observed in previous examples, optimal covalent binding was at 50% VDM.

EXAMPLE 9

The Time-Course for the Binding of Protein A to VDM-Grafted Membranes

Table 6 summarizes the results of several previous experiments in binding Protein A to grafted PE membranes in which length of incubation of the protein with the membrane was varied. Although the experimental conditions were not exactly comparable, they showed a trend that protein binding is highest if allowed to proceed overnight (16 h). An approximation of overnight binding can be obtained within one workday by incubating for at least 5.5 h.

TABLE 6

Time-Dependence of the Binding of Protein A to VDM-Grafted Membrane

| Example | Time (h) | Protein A Bound ($\mu g/cm^2$) |
|---|---|---|
| 4 | 1 | 3.2 |
| 7 | 5.5 | 5.6 |
| 6 | 16 | 6.2 |
| 5 | 16 | 7.0 |

These results, obtained from passive diffusion of protein into the membrane, demonstrated a definite time-dependence. A dramatic acceleration (perhaps a hundred-fold) would occur if protein were drawn into the membrane through some active process such as slight pressure differential.

EXAMPLE 10

The Effect of High Salt Concentration on Binding Protein A

Using the teachings, specifically Examples 1-35 of coassigned, copending U.S. patent application Ser. No. 07/609,436 (Coleman et al.), incorporated herein by reference (also published as PCT Publication WO 92/07879), it was investigated whether high sulfate concentration could also enhance the binding of protein to azlactone which had been E-beam grafted to PE membranes.

Protein A was incubated with various membranes for 19 h in 25 mM sodium phosphate, pH 7.5, 150 mM NaCl (low salt). In the "high salt" incubation 1.5M sodium sulfate was substituted for the sodium chloride. Controls were e-beam- and solvent-treated.

TABLE 7

The Effect of Sodium Sulfate on Protein Coupling to Grafted Membranes

| | Ratio of "High Salt" to "Low Salt" Binding | | |
|---|---|---|---|
| Membrane | Total Protein Bound ($\mu g/cm^2$) | SDS Resist. (%) | Coupled Protein ($\mu g/cm^2$) |
| Control | 9.5/5.3 | 30/20 | 2.8/1.0 |
| Control + 25% VDM | 10.5/5.8 | 45/30 | 4.8/1.8 |
| Control + 50% VDM | 9.4/4.9 | 55/34 | 5.1/1.6 |
| Control + 100% VDM | 6.6/2.7 | 70/58 | 4.6/1.5 |

The results are quite consistent with those observed with Protein A on hydrophilic azlactone-functionalized porous polymeric beads as shown in Examples 1-35 of U.S. Pat. No. 5,200,471. There was 2.5-3-fold increase in the amount of coupled protein, a 75-150% increase in total binding, and an increase in SDS resistance of 20-50%. Additionally these experiments confirmed conclusions drawn in earlier experiments: optimal VDM concentration is less than 100% and perhaps about 50%; the percentage of the binding which is SDS resistant continued to increase in proportion to the percentage of azlactone.

EXAMPLE 11

Azlactone-Grafted Membranes are Useful in an Immunodiagnostic

One of the major uses of specialized, biocompatible membranes in biotechnology is to immobilize one of the reactants in a clinical diagnostic test as in a heterogeneous ELISA-type assay. See for example, European Patent Publication 0 294 105 (Rothman et al.). In this example, it was demonstrated that an azlactone-functionalized membrane could be used to bind an antibody and that the resulting derivatized membrane could be used in a chromogenic ELISA (enzyme linked immunosorbent assay).

Strips of azlactone-functionalized membranes prepared according to Example 3 above were incubated with continuous rocking for 17 h at ambient temperature with either human IgG (hIgG in 100 mM NaCl and 100 mM sodium phosphate solution, pH 7.25) or bovine serum albumin (BSA), each at 1.0 mg/ml, in 10 ml of 25 mM sodium phosphate, 150 mM NaCl, pH 7.5. They were then given several 1 h rinses in buffer, dried, and stored, desiccated, at ambient temperature until used. Prior to use, to insure that all azlactone-functional moieties were reacted, membrane discs were incubated with 3.0M ethanolamine and 1 mg/ml BSA, pH 9.0, for 30 min., rinsed and used in the assay described below.

The assay was initiated by incubation of the discs with 10 ug/ml anti-human IgG-HRP (horseradish peroxidase) conjugate (Cappel-Worthington, Malvern, Pa.) for 1 h with continuous rocking. They were rinsed for 4 h, with rocking, with PBS-Tween (25 mM sodium phosphate, 0.6% Tween 20, pH 7.5) and transferred to clean test tubes for a chromogenic HRP substrate, o-phenylenediamine (Sigma Chem. Co.) (3 mM in 100 mM sodium citrate buffer, 0.12 mg 30% hydrogen peroxide, pH 5.0). The product of the peroxidation forms an orange-colored, partially-insoluble product after reaction with 2.5M $H_2SO_4$. Spectrophotometric estimations of the reaction were obtained by transferring 50 $\mu l$ of the reaction supernate to a 96-well microtiter plate containing 20 $\mu l$ of 2.5M $H_2SO_4$. Results of absorbance determinations at 490 nm on a microtiter plate spectrophotometer (Dynatech, Chantilly, Va.) are given in Table 8.

TABLE 8

Comparison of the Binding of Anti-IgG-HRP to Control and IgG-Containing Membranes

| | HRP Activity (mA @ 490/min) | | IgG/BSA |
|---|---|---|---|
| Sample | BSA-Treated | IgG-Treated | Ratio |
| 25% VDM | 98 | 451 | 4.9 |
| 50% VDM | 60 | 201 | 3.4 |
| 100% VDM | 41 | 199 | 5.5 |

In each case there is considerably more activity associated with the antibody-containing membranes than with the BSA controls.

In this example a 150,000 dalton antibody was immobilized, then complexed with a 200,000 dalton antibody-enzyme conjugate, indicating that there is not a great barrier to working with large protein complexes.

EXAMPLE 12

Gamma Irradiation Grafting of Hydrophilized Microporous Membrane with VDM and HEMA 15 preweighed pieces of PE microporous membrane, having a thin shell of poly(vinyl alcohol) prepared according to Example 22 of coassigned, copending application Ser. No. 08/122,807 (Gagnon et al.) and PCT Publication WO 92/07899, except that PE was used instead of PP, measuring 7.6×20.3 cm, were rolled-up and placed into glass ampules. The ampules were evacuated to pressures less than $2 \times 10^{-4}$ mm Hg and the glass necks were melt-sealed to prevent $O_2$ contamination. Three additional pieces were placed in unsealed test tubes. All 18 sample tubes were exposed to gamma irradiation for 9.5 hours for a total dose of 38 kGys. The 5 tubes had been placed side-by-side in a large envelope which was configured normal to the source, so that they would all be exposed to the same dose. The envelope was rotated 180° after about the first 4 hours of irradiation to further ensure that the samples were dosed evenly.

After gamma irradiation, the tubes were placed into a glove bag, which also contained the argon-purged (i.e., $O_2$-free) monomer solutions listed in Table 9 below. The glove bag was flushed with argon by 5 inflate/deflate cycles to remove as much $O_2$ as possible. Four sealed ampules were broken open, and the film samples within them were placed in either pure ethyl acetate (EtOAc), 10 wt/vol % VDM in EtOAc, or 10% VDM/25% HEMA in EtOAc, respectively, These were allowed to soak for longer than 5 minutes, before being removed from the solution and stored in stoppered test tubes. A total of three samples were prepared for each monomer solution. After all reactions were complete, the samples were removed from the glove bag and rinsed 3 times in fresh EtOAc to remove excess monomer, and air dried.

The membranes were analyzed for grafting add-on by weight uptake and by FT-IR spectroscopy. The weight uptake data showed that the 10% VDM and 10% VDM/25% HEMA membranes averaged about 0.7 and 1.0% wt. uptake. The IR spectra confirmed the wt. uptake data, showing significant absorbance at 1824 $cm^{-1}$ for VDM in both the 10% VDM and 10/25 VDM/HEMA samples. The samples also displayed an absorbance at 1670 $cm^{-1}$, indicative of partial hydrolysis of the VDM moiety. An additional absorption peak at 1728 $cm^{-1}$ for the 10/25 VDM/HEMA samples confirmed the incorporation of the HEMA monomer into the grafted copolymer. No 1728 $cm^{-1}$ peak could be seen in the 25% HEMA membranes. The wt. uptake data and the absorbance values for the VDM and HEMA functionalities, normalized to the PE absorbance peak at 1462 $cm^{-1}$, are tabulated below:

TABLE 9

| SAMPLE | AVE WT % ADD-ON | IR ABSORBANCE RATIO | |
|---|---|---|---|
| | | 1824 $cm^{-1}$/ 1471 $cm^{-1}$ | 1728 $cm^{-1}$/ 1471 $cm^{-1}$ |
| Control | 0.000 | 0.000 | 0.000 |
| γ only | 0.115 | 0.000 | 0.000 |
| γ in air | 0.160 | 0.000 | 0.000 |
| γ + EtOAc | 0.160 | 0.000 | 0.000 |
| γ + 10% VDM | 0.718 | 0.060 | 0.000 |
| γ + 10 VDM/ 25 HEMA | 1.013 | 0.040 | 0.120 |

Summing the IR absorbance ratios (including the 1670 $cm^{-1}$ peak) gives an indication of overall add-on.

EXAMPLE 13

E-beam Irradiation Grafting Hydrophilized Microporous Membrane with VDM and HEMA Pre-irradiation e-beam grafting of hydrophilized PE microporous membranes, prepared according to Example 3 above used the same equipment of Example 1 above, except that modifications were made to the glove box to minimize presence of $O_2$. An $O_2$ analyzer, installed in the glove box to monitor the $O_2$ concentration during the run, showed that these improvements allowed the $O_2$ concentration to be maintained at less than 30 ppm—often as low as 10 ppm.

Pieces of the membrane were taped to a polyethylene terephthalate (PET) carrier web and passed through an e-beam curtain at 6.1 m/min. The e-beam accelerating voltage was set at 150 KeV, and a dose rate of 50 kGys was used to irradiate the membranes. The samples came out of the e-beam chamber directly into a $N_2$ purged glove box where they were immersed in the monomer solution. The inert atmosphere helped to prevent quenching of the generated radicals with oxygen.

The solutions had concentrations (in wt %) VDM and HEMA in ethyl acetate in concentrations listed in Table 10 below.

Irradiated membrane samples were soaked in the monomer solution for 24 hours, followed by a three 5 minute soaks in fresh ethyl acetate in order to wash out excess monomer. They were then dried and placed in ziplock type bags to prevent possible hydrolysis of the azlactone by atmospheric water.

The membranes were incubated for 16 h with Protein A at 250 μg/ml in either 25 mM or 500 mM sodium phosphate buffer (pH 7.50) which was supplemented with 150 mM NaCl or 1.5M sodium sulfate. The results are presented in Table 10. Those experiments performed in the 25 MM buffer are indicated by an asterisk. All results are the averages of triplicates.

TABLE 10

Effects of Grafting HEMA in Combination with VDM into PE Membranes

| Sample (% VDM/HEMA) Salt | Initial Binding (μg/cm$^2$) Cl SO$_4$ | SDS Resistance (%) Cl SO$_4$ | Coupled Binding (μg/cm$^2$) Cl SO$_4$ |
|---|---|---|---|
| Untreated | 10.66/9.78 | 8/10 | 0.81/0.97 |
| Solvent | 11.57/10.29 | 21/31 | 2.38/3.18 |
| E-beam* | 11.97/9.52 | 23/30 | 2.72/2.86 |
| E-beam | 10.59/10.13 | 23/31 | 2.44/3.09 |
| 0/2.5* | 0.43/2.02 | 27/36 | 0.11/0.73 |
| 0/6.5* | 0.35/1.41 | 28/34 | 0.10/0.49 |
| 0/10 | 0.27/1.81 | 24/42 | 0.06/0.74 |
| 0/12.5 | 0.80/3.85 | 25/38 | 0.21/1.45 |
| 0/25* | 0.30/1.07 | 28/32 | 0.09/0.36 |
| 0/25 | 0.26/1.01 | 24/38 | 0.06/0.38 |
| 10/0* | 4.06/5.14 | 29/36 | 1.19/1.85 |
| 10/0 | 4.33/7.21 | 29/42 | 1.25/3.05 |
| 25/0* | 2.68/3.58 | 36/42 | 0.95/1.47 |
| 25/0 | 2.73/4.30 | 38/49 | 1.05/2.11 |
| 50/0 | 2.78/3.65 | 77/84 | 2.14/3.06 |
| 10/10 | 3.57/8.96 | 56/81 | 2.01/7.28 |
| 10/25* | 2.10/9.70 | 67/94 | 1.52/9.10 |
| 10/25 | 0.82/15.55 | 60/95 | 0.49/14.72 |
| 25/2.5* | 2.45/4.53 | 54/74 | 1.33/3.35 |
| 25/6.25* | 2.69/5.78 | 82/89 | 2.14/5.11 |
| 25/12.5 | 5.10/8.98 | 51/78 | 2.62/7.01 |
| 25/25 | 1.48/9.82 | 63/92 | 0.93/9.04 |
| 50/10 | 1.86/3.30 | 69/77 | 1.29/2.56 |

EXAMPLE 14

UV Initiated VDM Grafting on a Hydrophilized, Microporous Membrane

A piece of hydrophilic PE membrane prepared in the same manner as for Example 12 above was soaked with an ethyl acetate solution of 25 wt/vol % VDM in ethyl acetate +0.25% uv initiator azobis(isobutyronitrile) (commercially available as Irgacure ™ 907 from Ciba Geigy) and then fed into a $N_2$ purged RPL uv treater at 7.6 m/min. set at 21 amp lamp power (310 kW/m$^2$).

Another sample was treated the same way, except that the monomer solution also contained 2.5 wt % crosslinker (neopentylglycol diacrylate, NPGDA). Some evaporation of the monomer solution did occur prior to, and during the irradiation.

IR spectroscopy showed that VDM did indeed become grafted onto the membrane surfaces in both cases. Using the ratio of the IR absorbance for VDM at 1824 cm$^{-1}$ to the absorbance of PE at 1462 cm$^{-1}$ as a measure of VDM add-on, showed that the sample without the NPGDA had a greater add-on than that with the crosslinker.

EXAMPLE 15

Pre-Irradiation EB Grafting onto H-PP Membrane and PE BMF

Hydrophilic polypropylene (PP) membrane was prepared in the manner according to Example 22 of coassigned, copending U.S. patent application Ser. No. 07/775,969 (Gagnon et al.) published as PCT Publication WO 92/07899. PE blown microfiber (BMF) web was prepared according to Example 19 of Gagnon et al.), to become a calendared BMF nonwoven made from Dow 6808 LLDPE resin at a basis wt. of 94 g/m$^2$.

All samples of PP membrane and PE BMF nonwoven were irradiated in the manner according to Example 13 above with 50 kGys of 150 KeV e-beam irradiation prior to immersion in the monomer solutions listed in Table 11 in a <30 ppm O2 atmosphere. All monomer solutions, in ethyl acetate, had been purged with argon to remove O$_2$. Reaction was allowed to proceed for about 5 minutes prior to removal and rinsing in pure ethyl acetate.

The table below lists the grafting wt. % add-on, expressed as $$\frac{final\ wtw\ -\ initial\ wt}{initial\ wt} * 100$$

for the samples in terms of the monomer solution used.

TABLE 11

| E-beam Grafted VDM on PP Membrane and PE BMF | | |
|---|---|---|
| | WEIGHT PERCENT ADD-ON | |
| | PP-Membrane | PE-BMF |
| 10% VDM | 23% | 15% |
| 25% HEMA | 265% | 328% |
| 10/25 VDM/HEMA | 215% | 136% |

Infrared spectroscopy confirmed that these monomers were indeed incorporated onto the surfaces of these substrates as grafted polymers.

EXAMPLE 16

Preparation of and Protein Binding of Plasma VDM-Treated Materials

Hydrophilized, porous polyethylene (PE) membrane prepared according to Example 12 above was used without further treatment. Non-porous films of polypropylene (biaxially oriented, thermally extruded, 0.05 mm thick PP film), poly(ethyleneterephthalate) (biaxially oriented, 0.1 mm thick, PET film) and poly(tetrafluoroethylene) (0.05 mm thick PTFE film) were used without additional treatment.

Vinyldimethyl azlactone (VDM) was deposited onto all the film samples simultaneously in a glow discharge. The glow discharge depositions occurred in a belljar vacuum system using two parallel plate electrodes (20 cm×30 cm) spaced 5 cm apart. The film samples were placed on the lower electrode (grounded). The materials were subjected to a VDM glow discharge at 60 mtorr VDM pressure with a 15 W discharge power generated at a frequency of 25 kHz. First one side was treated, then the samples were turned over on the bottom electrode to treat the other side. The nominal thickness of the deposition was 70 nm on each side of the samples, as measured by a quartz-crystal-microbalance exposed to the discharge during the deposition.

Alternatively, the film samples were given an initial nitrogen-containing surface by nitrogen discharge prior to VDM deposition (noted in Table 12 below as "N/VDM" treatment). Prior to glow discharge deposition the samples were treated with nitrogen gas (200 mtorr) glow discharge of 15 W (25 kHz) for 10 s. This was followed by the VDM treatment as described above.

Triplicate (8 mm) discs of each material were cut using a standard office paper punch and placed in 2 mL micro centrifuge tubes followed by addition of 200 μL of the buffer solution containing radioiodinated Protein A (ranging from 2200 to 2500 cpm/ug of protein). The chloride buffer consisted of 150 mM NaCl and 500 mM sodium phosphate, pH 7.5; the sulfate buffer was 1.5M sodium sulfate and 500 mM sodium phosphate, pH 7.5. The discs were incubated with the solutions for 17 h (with continuous rocking) to allow the protein to fully equilibrate throughout the porous membrane. The coupling reaction was stopped by addition of 500 uL of 1.0M ethanolamine (in 25 mM sodium pyrophosphate, pH 9.0), twice for a total of 5 h. After three additional washes with the chloride buffer the discs were transferred to another test tube, and the associated radioactivity was determined using a Packard Model 5230 gamma radiation detector.

Protein which was resistant to solubilization by a treatment with the protein denaturant sodium dodecyl sulfate (SDS) was operationally defined as "covalently coupled" to the substrate. This treatment was with a 1% SDS solution (in 25 mM sodium phosphate buffer, pH 7.5) for 4 h at 37° C., followed by three washings with the warm SDS solution, and redetermination of the amount of associated radioactivity.

TABLE 12

| The Coupling of Protein to Plasma-Treated Materials | | | | |
|---|---|---|---|---|
| Material | Treatment | Protein Binding (μg/cm$^2$) Cl/SO$_4$ | SDS Resistance (%) | Protein Coupling (μg/cm$^2$) Cl/SO$_4$ |
| PE | Control | 11.2/9.5 | 33/34 | 3.7/3.2 |
| | VDM | 7.6/12.0 | 68/75 | 5.2/9.0 |
| | N/VDM | 7.9/20.6 | 79/83 | 6.2/17.0 |
| PP | Control | 0.6/0.4 | 21/17 | 0.1/0.1 |
| | VDM | 0.2/0.5 | 42/54 | 0.1/0.3 |
| | N/VDM | 0.9/0.7 | 75/69 | 0.7/0.5 |
| PET | Control | 1.4/0.8 | 27/20 | 0.4/0.2 |
| | VDM | 0.5/1.4 | 55/70 | 0.3/1.0 |
| | N/VDM | 0.4/1.1 | 62/65 | 0.2/0.7 |
| PTFE | Control | 0.4/0.3 | 22/17 | 0.1/0.1 |
| | VDM | 0.2/0.7 | 38/72 | 0.1/0.5 |
| | N/VDM | 0.3/1.2 | 56/76 | 0.2/0.9 |

Comparing just the Control samples, much more Protein A binds to the PE membrane than to any of the films. This is understandable because the membrane has about ten-fold more total surface area than the films.

Thus, it is quite surprising to observe a two-fold increase in the initial binding resulting from the nitrogen/VDM treatment, since the nitrogen treatment and VDM deposition do not penetrate substantially into the pores of the membrane. See Example 19 below. Actual enhancement of protein binding to PE is closer to the 400% observed for the PTFE films, than the 30% seen with the PET films. Such a high enhancement factor on PE membranes means that one might make a single-layer membrane act like a laminated, multi-layered membrane by surface treatment on one side to produce layer A, followed by treatment on the other side to produce layer C, followed by treatment with an e-beam or other penetrating activator to produce layer B. Layers A, B, and C might represent three different grafted monomers, conferring, e.g., different hydrophilicities or wettabilities, etc., or, perhaps, the three layers would use the same monomer, e.g., VDM, with which three different proteins or other ligands were immobilized to make, for example, a simple-to-use immunodiagnostic device.

EXAMPLE 17

Preparation of Corona-Treated Azlactone-Functional Supports

The corona deposition of samples (prepared according to Example 16) was carried out in a belljar system using two metal rollers (10 cm diameter, 15 cm long) for electrodes. The grounded electrode was covered with a 2 mm thick sleeve of silicone rubber and the electrodes were separated by a 1.7 mm gap. The samples were mounted on the silicone sleeve using tape. The rollers rotated at 25 rpm causing the samples to be repeatedly exposed to the discharge in the region of closest proximity between the two rollers. The belljar was evacuated to remove the air atmosphere and backfilled with 100 mtorr VDM and He to a pressure of 1 atm. The samples were exposed to a 250 W corona discharge (40 kHz) for 3 minutes of rotation (approximately 30 s actual exposure to the discharge).

Alternatively, similar to that described in Example 16, the samples were subjected to a nitrogen gas corona treatment (1 atm) of 250 W (40 kHz) for 15 s of rotation (2.5 s of exposure). This was followed by VDM treatment as described above. These samples are indicated in Table 13 as the N/VDM treatment.

The protein binding experiments were performed identically to those described in Example 16 except that the specific radioactivity of the Protein A was 1300–1700 cpm/μg of protein.

TABLE 13

| | The Coupling of Protein to Corona-Treated Materials | | | |
|---|---|---|---|---|
| Material | Treatment | Protein Binding (μg/cm$^2$) Cl/SO$_4$ | SDS Resistance (%) | Protein Coupling (μg/cm$^2$) Cl/SO$_4$ |
| PE | Control | 13.8/10.5 | 35/32 | 4.8/3.3 |
| | VDM | 14.8/23.0 | 81/86 | 12.0/19.8 |
| | N/VDM | 12.7/8.8 | 78/77 | 9.9/6.9 |
| PP | Control | 1.2/0.4 | 15/15 | 0.2/0.1 |
| | VDM | 1.9/1.0 | 58/40 | 1.1/0.4 |
| | N/VDM | 2.0/1.0 | 66/45 | 1.4/0.5 |
| PET | Control | 1.8/0.8 | 24/19 | 0.4/0.2 |
| | VDM | 1.9/0.9 | 49/36 | 0.9/0.3 |
| | N/VDM | 1.3/0.8 | 62/44 | 0.8/0.3 |
| PTFE | Control | 0.6/0.4 | 17/15 | 0.1/0.1 |
| | VDM | 1.5/0.8 | 70/57 | 1.0/0.5 |
| | N/VDM | 1.3/1.0 | 72/64 | 1.0/0.6 |

TABLE 13-continued

Corona treatment yields results very similar to those observed in Example 16 with plasma treatment. There are differences in the absolute values of some of the numbers, but the general affect is the same: addition of azlactone functionality to the surface results in an increase in the amount of coupled protein.

In the event that it were desired to graft azlactone-functionality to interior surfaces of a porous, pre-existing support, one could shield both electrodes with silicone rubber sleeves (like that described above) and employ the same corona discharge procedure using helium as described in this Example to achieve a penetrating VDM treatment.

EXAMPLE 18

The Preparation of and Protein Binding to Plasma VDM-Treated Porous and Fibrous Substrates VDM was deposited onto the following materials in a glow discharge procedure as described in Example 16:

PP blown microfiber web (basis weight of 60 g/m$^2$ and fiber diameter of 5–10 μm) prepared by melt-blowing techniques disclosed in van Wente et al. "Superfine Thermoplastic Fibers" *Industrial Engineering Chemistry*, Vol. 48, pages 1342 et seq. (1956) and van Wente et al "Manufacture of Superfine Organic Fibers" Report No. 4364 of Naval Research Laboratories (May 25, 1954);

Celgard ™ microporous polypropylene membrane 2402 (commercially available from Hoechst-Celanese, Charlotte, N.C.);

Polyurethane commercially available from Dow Chemical under the tradename "Pellethane 2363-65D".

Rayon blown microfiber web, such as that used in Micropore ™ tape, commercially available from Minnesota Mining and Manufacturing Company; and The PP film and hydrophilized porous PE membrane treated in the manner described in Example 16.

The non-porous PP film was also subjected to simultaneous treatment with a combination of VDM and hydroxyethyl methacrylate (HEMA) using a glow discharge (50 mtorr VDM, 10 mtorr HEMA, 15 W) to deposit a 70 nm coating.

Protein binding experiments were performed as described in Example 16, except that the blown microfiber web and Celgard materials required 0.2% Triton X-100 in order to be thoroughly wetted by the buffer solutions.

The specific radioactivities varied from 5100 to 6500 cpm/μg of protein. The ethanolamine quenching steps were for a total of 3 h.

TABLE 14

The Coupling of Protein to Plasma-Treated Materials

| Material | Treatment | Protein Binding ($\mu g/cm^2$) Cl/SO$_4$ | SDS Resistance (%) | Protein Coupling ($\mu g/cm^2$) Cl/SO$_4$ |
|---|---|---|---|---|
| PP | Control | 0.37/0.26 | 6/9 | 0.02/0.02 |
|  | VDM | 0.17/0.77 | 23/76 | 0.04/0.58 |
|  | VDM/HEMA | 0.16/0.79 | 23/80 | 0.04/0.63 |
| PE | Control | 3.50/6.48 | 45/62 | 1.57/4.00 |
|  | VDM | 1.77/16.10 | 86/91 | 1.54/14.71 |
| Rayon | Control | 0.06/0.17 | 26/40 | 0.02/0.07 |
|  | VDM | 0.08/1.33 | 34/91 | 0.03/1.22 |
| PU | Control | 0.30/0.33 | 29/38 | 0.09/0.12 |
|  | VDM | 0.19/0.68 | 47/64 | 0.09/0.44 |
| PP/BMF* | Control | 0.03/0.27 | 13/15 | 0.004/0.04 |
|  | VDM | 0.03/3.91 | 25/93 | 0.009/3.65 |
| Celgard* | Control | 0.03/0.93 | 9/18 | 0.003/0.17 |
|  | VDM | 0.04/1.10 | 19/68 | 0.007/0.75 |

*indicated Triton X-100 in protein incubation solution

Azlactone-modification of rayon (a cellulose-based synthetic polymer) and PU yield 17-fold and four-fold protein coupling increases, respectively. The PP microfiber shows a tremendous hundred-fold increase upon azlactone modification. The modification of Celgard polyethylene is especially useful because Celgard polyethylene is often a material used to make microporous hollow fiber filtration membranes. Addition of a pleotropic agent such as azlactone to hollow fiber membranes would increase their utility many fold.

COMPARISON EXAMPLE 19

Glow Discharge Treatment Does Not Penetrate into Porous Material

Two 10 cm × 10 cm pieces of microporous PE membrane, 20 $\mu$m thick, prepared according to Example 23 of U.S. Pat. No. 4,539,256 (Shipman) were taped together along their edges and placed on the bottom electrode for plasma glow discharge treatment in the belljar vacuum system according to Example 16. The membrane was treated with a glow discharge of VDM (60 mTorr), as described in Example 16. Two samples were prepared, one with a 70 nm coating and the other with a 150 nm coating of the VDM-plasma polymer. After treatment, the upper layer of the two-layer construction was separated from the lower layer, and analyzed by X-ray photoelectron spectroscopy (XPS). Both surfaces of this membrane, the top surface (exposed to the electrical discharge) and the bottom surface (which was in contact with the lower membrane), were analyzed.

TABLE 15

XPS Analysis of the External Surfaces of Discharge-Treated 20 $\mu$m Porous Membranes

| Sample | Atomic Ratios | |
|---|---|---|
|  | O/C | N/C |
| 70 nm - top | 0.23 | 0.12 |
| 70 nm - bottom | 0.0 | 0.0 |
| 150 nm - top | 0.22 | 0.12 |
| 150 nm - bottom | 0.0 | 0.0 |

The top surfaces clearly have azlactone-functionality, as evidenced by the oxygen and nitrogen atom content. The bottom surfaces of the membranes are untreated PE, with no oxygen or nitrogen present. This demonstrated that the electrical-discharge-deposited polymer of VDM does not penetrate appreciably into the pores of the membrane, even a very thin membrane and even when very heavily loaded with VDM (as evidenced by the ratios of O and N to C which are very near the theoretical values expected for an "infinitely thick" layer of pure VDM, 0.29 and 0.14, respectively). This experiment demonstrated the feasibility of the "multi-layered" single membrane devices discussed in Example 16.

EXAMPLES 20-51

Crosslinked Azlactone-functional Coatings on Nonwoven Polymeric Supports

Table 16 below shows the results of a series of experiments to prepare crosslinked azlactone-functional coatings on surfaces of nonwoven polymeric supports. The methods of preparation follow Table 16.

TABLE 16

Azlactone - Functional Coatings
COATED NONWOVENS TABLE

|  | MONOMER FORMULATION | NONWOVEN | % SDS RES. | COUPLED PROTEIN A $\mu g/cm^2$ |
|---|---|---|---|---|
| 20 | 20:20:60 | REEMAY-2 | 93 | 21.17 |
| 21 | EGDMA/VDM/HEMA | REEMAY-1 | 68 | 1.45 |
| 22 | (50 g in 400 mL IPA) | PET TB | 86 | 11.04 |
| 23 |  | PET LB | 82 | 7.70 |
| 24 |  | PP OE | 53 | 1.77 |
| 25 |  | PUR | 74 | 3.02 |
| 26 |  | COTTON | 89 | 20.53 |
| 27 | 80:20 TMPTMA/VDM | CEREX | 75 | 3.70 |
| 28 | 50 g in 400 mL Hexanes | PET CW | 65 | 2.91 |
| 29 |  | DUPONT SONTARA | 85 | 9.53 |
| 30 |  | PE/PP-3 | 64 | 65.20 |
| 31 |  | PE/PP-10 | 37 | 16.66 |
| 32 | 70:20:10 | DUPONT SONTARA | 68 | 1.43 |
| 33 | BA/VDM/TMPTMA | CFX NYLON | 70 | 1.79 |
| 34 | (50 g in 400 mL | PP | 52 | 0.29 |
| 35 | Hexanes) | RAYON | 73 | 2.06 |
| 36 |  | PP NP | 26 | 1.07 |
| 37 | 70:20:10 | DUPONT SONTARA | 81 | 2.71 |
| 38 | BA/VDM/EGDMA | CFX NYLON | 69 | 2.09 |
| 39 | (50 g in 400 mL | PP | 33 | 0.27 |
| 40 | Hexanes | RAYON | 77 | 9.92 |
| 41 |  | PP NP | 4 | 0.23 |
| 42 | 70:20:10 IOA/VDM/EGDMA | DUPONT SONTARA | 66 | 1.38 |
| 43 | (500 g in 400 mL Hexanes) | CFX NYLON | 72 | 1.37 |
| 44 |  | PP | 36 | 0.21 |

TABLE 16-continued

| | | | |
|---|---|---|---|
| 45 | | RAYON | 75 | 1.28 |
| 46 | | PP NP | 32 | 1.04 |
| 47 | 50:20:20:10 | DUPONT SONTARA | 74 | 1.19 |
| 48 | IBMA/BMA/VDM/TMPTMA | CFX NYLON | 63 | 1.27 |
| 49 | (50 g in 400 mL Hexanes) | PP | 49 | 0.30 |
| 50 | | RAYON | 76 | 2.49 |
| 51 | | PP NP | 34 | 2.37 |

| | |
|---|---|
| PROTEIN A | protein A coupled using 1.5M sulfate in 0.2M sodium phosphate buffer |
| REEMAY-1 | Style 2200 spunbonded polyester from REEMAY of Old Hickory, Tennessee |
| REEMAY-2 | Style 2295 spunbonded polyester from REEMAY |
| DUPONT SONTARA | Rayon/polyester (basis weight 135 g/m$^2$ from DuPont) |
| CEREX | Type 23 Nylon 66 (basis weight 34 g/m$^2$) from Fiberweb of Simpsonville, S.C. |
| PET TB | Thermal bonded polyester prepared from CELLBOND branded bicomponent fiber (25μ fiber diameter) on air laid web former from Rando Machine and using air circulation oven for binding |
| PET LB | Air laid polyester bonded with Rohm and Haas branded latex |
| PP OE | Oriented, embossed polypropylene (8μ fiber diameter)melt blown according to U.S. Pat. No. 4,988,560 (Meyer et al.) |
| PUR | Melt blown polyurethane (8μ fiber diameter) melt blown according to Wente et al. "Superfine Thermoplastic Fibers" in Industrial Engineering Chemistry, Vol. 48, page 1342 et seq. (1956) |
| COTTON | Spunlaced cotton from Veratec Corporation |
| PET CW | Mechanically laid, embossed polyester having 2 denier fiber |
| PE/PP-3 | Needlepunched, air laid polyethylene sheathed polyproyene having 3 denier fiber |
| PE/PP-10 | Needle punched, air laid polyethylene sheathed polypropylene having 10 denier fiber |
| CFS Nylon | Melt blown CFX nylon copolymer from Allied |
| PP NP | Needlepunched, air laid polypropylene having 205 g/m$^2$ basis weight |
| PP | Air laid polypropylene having 205 g/m$^2$ basis weight |
| RAYON | Needlepunched, air laid rayon having 135 g/m$^2$ basis weight |

EXAMPLES 20

20:20:60 EGDMA/VDM/HEMA Coating on Spunbonded Polyester

A spunbonded polyester sample (REEMAY, style 2200; 15 cm square) was dipped into a 2-propanol solution of 20 parts EGDMA, 20 parts VDM and 60 parts HEMA (prepared by dissolving 10.0 g EGDMA, 10.0 g VDM, 30.0 g HEMA, and 1.0 g Darocure 1173 in 400 ml 2-propanol), and then pressed between sheets of polyethylene to remove excess solution. After purging the sample with N$_2$ for 3 minutes, the monomer coating was polymerized by exposure, under N$_2$, to low intensity UV irradiation for 12 minutes. The support was then soaked in 2-propanol for 1 minute and air dried. Analysis by attenuated total reflectance IR (ATIR) revealed the characteristic azlactone carbonyl absorption at 1820 cm$^{-1}$ indicating azlactone incorporation in the polymer coating. SEM analysis of the treated polyester revealed no particulates and indicated a uniform coating of the fibers. The azlactone-functional spunbonded polyester support coupled 21.17 μg of radiolabeled Protein A per cm$^2$ (measured after SDS treatment).

EXAMPLES 21, 23–26

The nonwoven samples 21 and 23–26 were coated and cured in the same manner as Example 20 except a different nonwoven was employed, as identified in Table 16.

EXAMPLE 22

20:20:60 EGDMA/VDM/HEMA Coating on Thermal Bonded Polyester

The thermal bonded polyester sample (25 μm thick, 15 cm square) was coated and cured in the manner of Example 1. Analysis of the finished support by ATIR revealed the azlactone carbonyl absorption at 1820 CM$^{-1}$. SEM analysis revealed the coating to be grainy and particulate. The thermal bonded polyester azlactone-functional support coupled 11.04 μg of radiolabeled Protein A per cm$^2$ (measured after SDS treatment).

EXAMPLE 30

80:20 TMPTMA/VDM Coating on Polypropylene

A polypropylene sample (3 denier, needle punched, 15 cm square) was dipped into a hexane solution of 80:20 TMPTMA/VDM (prepared by dissolving 40.0 g TMPTMA, 10.0 g VDM, and 1.0 g Darocure 1173 in 400 mL hexane). Excess solution was removed from the web by pressing it between sheets of polyethylene. After purging with N$_2$ for 3 minutes, the monomer coating was polymerized by exposure under N$_2$, to low intensity UV irradiation for 13 minutes. Because of the thickness of this sample, the web was flipped over, purged, and irradiated for an additional 6 minutes. The azlactone-functional support was then rinsed with hexane and air-dried. SEM analysis of the composite revealed a grainy particulate coating with some agglomerated particles. The Daiwa composite coupled 65.2 μg of radiolabled Protein A per cm$^2$ (measured after SDS treatment).

EXAMPLES 27-29 AND 31

The nonwoven samples of Examples 27-29 and 31 (15 cm square) were coated and cured in the manner of Example 30, except that Examples 27-29 were irradiated on one side only for 8-11 min. and Example 31 was irradiated on both sides in succession for 7 min each.

EXAMPLES 32-36

The nonwoven samples of Examples 32-36 were dipped into a hexanes solution of 70 parts BA, 20 parts VDM, and 10 parts of TMPTMA, (prepared by dissolving 35.0 g BA, 10.0 g VDM, 5.0 g TMPTMA, and 1.0 g Darocure 1173 photoinitiator in 400 ml of hexanes) and then were pressed between sheets of polyethylene to remove excess solution. After purging with $N_2$ for 3 min., the monomer coating was polymerized by exposure under $N_2$, to low intensity uv radiation for 10 mins. The azlactone-functional supports were soaked and rinsed with hexanes and then dried under $N_2$.

EXAMPLES 37-46

The nonwoven samples of Examples 37-46 (10 cm square) were coated with a hexanes solution of 70 parts BA, 20 parts VDM, 10 parts EGDMA, containing 2% Darocure™ 1173 photoinitiator and then cured in the manner of Examples 32-36.

EXAMPLES 47-51

The nonwoven samples of Examples 47-51 (10 cm square) were coated with a hexanes solution of 50 parts IBMA, 20 parts BMA, 20 parts VDM, 10 parts TMPTMA, containing 2% Darocure™ 1173 and then cured with 12 minutes of irradiation in the same manner as Examples 32-36.

EXAMPLE 52

Preparation of Azlactone-Functional Polymethylmethacrylate

Poly(methylmethacrylate) (PMMA commercially available as Perspex CQ, UV from ICI) buttons were exposed to one of several electron beam dosages: grafting at conditions of 10, 20, 30, 50, or 100 kGys discharged at 100 kV in $N_2$ gas a flow of less than 4 scm/min, at a line speed of 9.2 m/min, with $O_2$ content less than 50 ppm. The activated PMMA substrate was immediately transferred into VDM monomer for grafting. The grafting was immediately started on the surface of the support. The buttons were washed with VDM monomer and anhydrous ethyl-ether. When the activated support was immersed longer (e.g., several hours), in VDM monomer, the VDM-grafted PMMA was dissolved in the VDM monomer. Therefore, to minimize dissolution, a heptane/VDM (75/25 wt. %) solution was substituted for VDM monomer. It was found that the surface of the button support remained intact. As a control, the PMMA buttons were exposed to electron beam only to see how much polymeric chains were degraded by electron beam. Evidence of VDM grafting on the PMMA button was confirmed by ATR-FTIR, $^{13}C$ NMR and XPS (ESCA). The molecular weight distribution curve indicated there was no degradation of the polymeric chains of the support at all under the conditions of 10 kGys electron beam dose.

EXAMPLE 53

Azlactone-functional PMMA Prepared and Reacted with Amine-Terminated Heparin.

PMMA casted film (Perspex, CQ, UV; <0.1 mm thickness) was exposed to the electron beam in a $N_2$ blanket, and then conveyed into the glove box under $N_2$ gas where the activated film was immersed in VDM monomer for twelve hours at room temperature. The film lost all of its original shape but was not dissolved in the VDM solution. The VDM monomer was decanted and the grafted PMMA dissolved in chloroform and precipitated into hexane. This step was repeated two times to remove ungrafted VDM monomer. Finally, the azlactone-functional PMMA support was dissolved in chloroform, casted onto an aluminum plate, and peeled away from the plate to form a thin film for analysis. Transmission IR spectrum of the grafted PMMA showed there was a strong peak of carbonyl group of VDM at 1820 cm$^{-1}$.

To prepare amine-terminated heparin, 1 g of heparin (commercially available from Diosynth) was dissolved in 300 mL of water. 10 mg Sodium Nitrite was added to the solution and adjusted the pH to 2.7 with 1N hydrochloric acid. The solution was adjusted to 7.0 and dialyzed against 3 L of water in 3500 molecular weight cut-off dialysis tubing. The solution was concentrated and lyophilized to produce heparin-aldehyde.

1 g of heparin-aldehyde was dissolved in 100 mL of the buffer solution (1% citrate, 0.9% sodium chloride, pH=6.5). 0.5 g of ammonium sulfate and 0.25 g of sodium cyanoborohydride were added to the solution and stirred for five hours at room temperature. The solution was dialyzed with 3500 molecular weight cut-off dialysis tubing against water. The solution was concentrated and lyophilized to produce amine-terminated heparin.

Then, to react amine-terminated heparin with azlactone-functional PMMA, the film prepared according to this example was reacted with a solution of 0.25 g of amine-terminated heparin which was dissolved in 50 mL of buffer solution (pH=8.8), and stirred for several hours at room temperature. The heparinized-film was rinsed with water and dipped in 1% solution of toluidine blue (Sigma Chemical) in water for staining. The film stained a violet color within a few minutes to show heparin was attached to the film.

EXAMPLE 54

Azlactone-functional PMMA Prepared in Heptane

PMMA casted film (Perspex C.Q./uv from ICI; less than 0.1 mm thickness) and a PMMA button (2.75 mm thickness) were both exposed to electron beam (10 kGys at 120 kV) in a $N_2$ blanket and then conveyed into the glove box under $N_2$ gas where the activated film and the activated button were both immersed in a mixture of heptane/VDM (75/25 wt. %) at room temperature and 45° up to 15 hours. After grafting, both forms of the VDM-grafted PMMA were washed with anhydrous ethyl-ether. ATR-FTIR spectra of the VDM-grafted PMMA showed there was a strong peak of carbonyl group of VDM at 1820 cm$^{-1}$.

EXAMPLE 55

Azlactone-functional PMMA Prepared with Corona Discharge

The corona-discharge assembly of Example 17 above was placed in a glove box filled with $N_2$ gas. PMMA films (from ICI and less than 0.1 mm thickness) were exposed to corona-discharge in different conditions at 150 to 300 watts for 0.4–4 seconds exposure discharged at 62 kHz (at 150 watts for 0.4 and 4.0 secs.; at 200 watts for 1.2 and 4.0 secs.; and at 300 watts for 1.2 and 4.0 secs. The activated PMMA films were immersed in heptane/VDM mixture (75/25 wt. %) at room temperature for 2 hours. Evidence of VDM grafting was observed by ATR-FTIR. In these instances, there was no evidence of molecular weight degradation. From studying these examples 52–55 and the prior examples forming biologically active and useful adduct supports, it is possible to convert a hydrophobic PMMA useful as an intraocular lens into a hydrophilic PMMA coated with an anticoagulant or other biocompatible hydrophilic and/or biologically active material by reaction of azlactone-functional moieties with an anticoagulant or another nucleophile-terminated hydrophilic moiety.

EXAMPLE 56

Dispersion Polymerization of Azlactone-Functional Particles in Polyethylene Membranes Three microporous PE membranes prepared according to Example 23 of U.S. Pat. No. 4,539,256 (Shipman) and one hydrophilized microporous PE membrane prepared according to Example 22 of copending, coassigned application Ser. No. 07/775,969 (Gagnon et al.), each having a size of 15 cm×15 cm, were each placed on a slightly larger piece of dense PE film and were saturated with a solution containing 10 g of VDM; 10 g of ethylene glycol dimethacrylate (EGDMA); 30 g of 2-hydroxyethylmethacrylate (HEMA); 1 g of photoinitiator (Darocure 1173 commercially available from E Merck), and 400 ml of isopropyl alcohol (net solids of 11.1 wt. %). Another piece of dense PE film was then placed on top of the saturated membrane followed by rubbing the "sandwich" construction to remove any excess solution. The sandwich construction was place in the bottom of a $N_2$ purged box having a Pyrex brand glass top, and the sandwich construction was irradiated through the Pyrex window using two fluorescent UV "black" lights having emissions at a maximum of 360 nm. The three PE samples were irradiated for 5 min, 10 min, and 15 min, respectively. The hydrophilized PE sample was irradiated for 10 min. Following irradiation, the sandwich constructions were removed from the box, separated from the PE film sheets. Except for the PE sample irradiated for 10 min, which was directly rinsed with isopropyl alcohol, each sample was dried and then rinsed with isopropyl alcohol for 10 min. Scanning electron microscopy (SEM) of the surface and cross-section of each sample was performed. Except for the hydrophilized PE sample, SEM observation of cross-sections showed numerous particles and particle clusters. Individual particles were seen between 0.4 and 0.8 µm in diameter. However, many particles were also agglomerated into a mass which was large as 5 µm in diameter. On the surface of these samples was a 2–5 µm thick cake of agglomerated particles having average diameters of about 0.6 µm, and on the surface of all samples but the PE sample rinsed before drying, there were areas of a dense skin layer of about 1–2 µm thick on the outside surface. The PE sample rinsed directly was skin-free and had many particles trapped within the void spaces throughout the membrane cross-section. The hydrophilized PE sample was mostly skinned and contained few if any particles within the cross-section. The interior of this membrane appeared to have a rough coating on the fibril surfaces. Infrared spectroscopy of the PE sample rinsed directly showed strong absorbances at 1822 cm$^{-1}$ and 1671 cm$^{-1}$ (indicating VDM) and at 1728 cm$^{-1}$ (HEMA and EGDMA) which confirmed the presence of crosslinked VDM/HEMA copolymer.

EXAMPLE 57

Dispersion Polymerization of Azlactone-functional Particles in Polypropylene Membrane A microporous PP membrane (prepared according to Example 9 of U.S. Pat. No. 4,726,989 (Mrozinski)) was treated in the same manner as the hydrophilized PE membrane in Example 55. In this instance, the sample was skin-free and had many particles trapped within the void spaces throughout the membrane cross-section.

EXAMPLE 57

Dispersion Polymerization of Azlactone-functional Particles with a Stabilizer The procedure of Example 55 was repeated with the addition of 2.23 wt./vol % of poly(vinyl pyrrolidone) (PVP K-30 commercially available from EM Sciences) to the monomer mixture of Example 55 and saturated into the pores of a PE membrane prepared according to Example 23 of 4,539,256 (Shipman). After irradiation, isopropyl alcohol rinsing was employed. For comparison, the same PE membrane was saturated with the mixture of Example 55. Without PVP stabilizer, a bimodal distribution of particles measuring about 0.15 µm in diameter were found within the pores of the PE membrane with a few 2.0 µm diameter particles sparsely scattered through the sample. With the PVP present in the monomer mixture, the particles were about 0.2–0.5 µm with no occurrence of the much larger particles. Thus, PVP stabilizer improves the particle size distribution particles within void spaces of the PE membrane.

EXAMPLES 58–65

Dispersion Polymerization without Alteration of the Support Beyond Usefulness PP membranes samples prepared according to Example 9 of U.S. Pat. No. 4,729,989 (Mrozinski) were used as the outer layers in a three layer membrane stack, having a middle layer of a hydrophilized PE membrane prepared according to Example 23 of U.S. Pat. No. 4,539,256 (Shipman) and hydrophilized according to Example 22 of copending, coassigned application Ser. No. 07/775,969 (Gagnon et al.) The hydrophilized middle layer is denominated the H-PE layer. The membrane stack was placed upon a piece of dense LDPE film and saturated with a monomer solution of 0.79 moles VDM, 0.48 moles EDGMA, 0.25 moles HEMA, containing 2% Darocure 1173 photoinitiator, dissolved in isopropyl alcohol in the amount of percent solids shown in Tables 17 and 18 below, according to their theoretical percent solids. Examples 58–61 were the top layer of PP in each sample; Examples 62–65 were the middle layer, H-PE, in each sample. (Unmodified controls were also tested.)

After saturation, another piece of dense LDPE film was placed to cover the membrane stack, and the excess solution was squeezed out with a rubber roller. The membrane stack and the cover LDPE films were then irradiated for 20 minutes with a bank of 4 fluorescent "black lights" having an emission maximum at 360 nm, under ambient temperature, pressure, and atmosphere.

Samples of Examples 58–65 were subjected to BET analysis (using the method described in Example 3 above), and pore size analysis, Gurley analysis, porosity, and water permeability analysis (using the methods described in PCT Publication WO 92/07899 (Gagnon et al.)). The results for surface area are shown in Table 17; the porous property results are shown in Table 18. Examples 58–61 show that where distinct dispersion beads develop within the pores of the membrane, the surface area is significantly enhanced. This enhancement is surprisingly obtained without a significant decrease of other microporous properties of the membranes, as seen in Table 18.

By contrast, the results of Examples 62–65 show that a coating of crosslinked VDM-co-HEMA is formed in situ on the internal pore surfaces. This is shown by a decrease in specific area/frontal surface area ratio, with the exception being Example 65, which had a "lacy" network of crosslinked dispersion beads filling the pores of the middle layer H-PE. Also in contrast to particulate additions, coatings of Examples 62–64 served to decrease somewhat the flow through properties (see Gurley and water permeability properties) of the membrane, although the pore size, thickness, and porosity values were not similarly affected beyond usefulness of the azlactone-functional support.

TABLE 17

SURFACE AREA OF DISPERSION POLYMERIZED SAMPLES

| Example | Monomer Solution (% Solids) | Area/Mass ($m^2/gr$) | Wt Add On (%) | Basis Wt. ($gr/m^2$) | Total Area/Surface ($m^2/m^2$) | % Change in Area/Surface |
|---|---|---|---|---|---|---|
| PP Control | — | 20.9 | 00.0 | 16.000 | 334.40 | — |
| 58 | 2.8 | 23.9 | 1.50 | 16.240 | 388.14 | 16.1 |
| 59 | 5.7 | 25.6 | 9.90 | 17.584 | 450.15 | 34.6 |
| 60 | 11.3 | 15.0 | 41.00 | 22.560 | 338.40 | 1.2 |
| 61 | 22.6 | 17.2 | 57.60 | 25.216 | 433.72 | 29.7 |
| H-PE Control | — | 18.4 | 0.00 | 14.700 | 270.48 | — |
| 62 | 2.8 | 17.2 | 0.90 | 14.832 | 255.12 | −5.7 |
| 63 | 5.7 | 13.8 | 11.30 | 17.920 | 247.30 | −8.6 |
| 64 | 11.3 | 9.8 | 25.80 | 21.800 | 213.64 | −21.0 |
| 65 | 22.6 | 10.5 | 44.00 | 32.700 | 343.35 | 26.9 |

TABLE 18

POROUS PROPERTIES OF DISPERSION POLYMERIZED SAMPLES

| Example | Monomer Solution (% Solids) | Thickness ($\mu m$) | Pore Size ($\mu m$) | Gurley Wt. (sec/50 cc) | Porosity (%) | Water Permeability ($ml/min/cm^2$) Area/Surface |
|---|---|---|---|---|---|---|
| PP Control | 0.0 | 51 | 0.47 | 10 | 77.6 | 6.34 |
| 58 | 2.8 | 53 | 0.56 | 11 | 73.6 | 8.66 |
| 59 | 5.7 | 58 | 0.51 | 12 | 74.0 | 7.43 |
| 60 | 11.3 | 58 | 0.51 | 16 | 66.1 | 4.93 |
| 61 | 22.6 | 91 | 0.49 | 14 | 75.5 | 4.82 |
| H-PE Control | 0.0 | 61 | 0.47 | 33 | 71.4 | 3.68 |
| 62 | 2.8 | 53 | 0.62 | 21 | 69.7 | — |
| 63 | 5.7 | 56 | 0.57 | 62 | 61.8 | 1.46 |
| 64 | 11.3 | 69 | — | >300 | 66.8 | — |
| 65 | 22.6 | 61 | 0.47 | >300 | 66.4 | <0.70 |

Examples 63–65 were also subjected to testing for protein coupling analysis. The samples were tested using radioactively labeled protein A, according to the procedures of Examples 5, 6 and 10 above by incubating overnight in radiolabeled Protein A, buffered with either 1.5M sulfate buffer (SO4) or 250 mM phophate buffered saline (PBS), both at pH 7.5. After quenching of unreacted azlactone moieties with ethanolamine and repeated rinsing in buffer, scintillation counting was done to determine initial binding levels. The samples were then incubated for 4 hours in 1.0% sodium dodecylsulfate (SDS), followed by scintillation counting to determine the amount of coupled protein remaining. Table 19 shows the results.

TABLE 19

PROTEIN BINDING PROPERTIES OF DISPERSION POLYMERIZED SAMPLES

| Example | Wt. Add On (%) | Area/Surf* ($m^2/m^2$) | Buffer Type | Protein Binding ($\mu g/cm^2$) | SDS Res. (%) | Protein Coupling ($\mu g/cm^2$) |
|---|---|---|---|---|---|---|
| PP Control | 0.00 | 270.48 | SO$_4$ | 21.1 | 27.6 | 5.8 |
| 63 | 11.30 | 247.30 | SO$_4$ | 38.1 | 79.6 | 30.3 |
| 64 | 25.80 | 231.64 | SO$_4$ | 16.7 | 86.0 | 14.2 |
| 65 | 44.00 | 343.35 | SO$_4$ | 48.6 | 87.6 | 42.3 |
| H-PE Control | 0.00 | 270.48 | PBS | 21.2 | 30.6 | 6.5 |
| 63 | 11.30 | 247.30 | PBS | 15.1 | 63.0 | 9.6 |
| 64 | 25.80 | 213.64 | PBS | 6.7 | 58.8 | 4.0 |

TABLE 19-continued

PROTEIN BINDING PROPERTIES OF DISPERSION POLYMERIZED SAMPLES

| Example | Wt. Add On (%) | Area/Surf* (m²/m²) | Buffer Type | Protein Binding (μg/cm²) | SDS Res. (%) | Protein Coupling (μg/cm²) |
|---|---|---|---|---|---|---|
| 65 | 44.00 | 343.35 | PBS | 5.5 | 60.2 | 3.3 |

*See Table 17 above.

These data show that the addition of azlactone functionality does correlate with an increase in the percent of coupled protein, and that use of sulfate is preferred to use of saline as a buffer system.

The experiment was repeated for samples of Example 63, except that the experiments were done as a function of the time allowed for initial binding. The amount of time ranged from 0.5 hours to 16 hours and resulted in initial binding ranging from 21 μg/cm² for 0.5 hours to 48.9 μg/cm² for 16 hours.

The experiment was then repeated for samples of Example 63, except that rather than incubating in the protein A solution, the protein A solution was flowed through the azlactone-functional membrane. In this case, 3 ml of a 1 mg/ml solution of non-radioactive, $SO_4$-buffered protein A solution at pH=7.5 was suctioned through a 25 mm disk of the azlactone-functional membrane using aspirator vacuum. After three flow-through rinse cycles with PBS buffer solution and quenching of possible unreacted azlactone moieties with 6 ml of 1M ethanolamine (buffered to pH=9 with 25 mM pyrophosphate), the membrane samples were analyzed for Protein A content using the BCA protocol published by Pierce Chemical Co. for BCA Protein Assay Reagent (Cat. No. #3220/23225, Pierce Chemical Co., Rockford, Ill.). It was found that the membranes initially bound an average of 22.3 μg/ml of protein A using the flow-through mode of binding, where the time of exposure to the protein solution was less than about 3 minutes. This amount of initial binding was consistent with initial binding levels for Example 63 using a 0.5 hour incubation. The advantage of flow-through binding is that binding is not limited by the rate of diffusion of protein into pores of the membrane. Flow-through binding also demonstrated that kinetics of initial binding of protein to azlactone moieties is apparently very rapid.

EXAMPLE 66-69

Retained Useful Porous Properties of Azlactone-functional Supports

Membranes were prepared according to Example 3 above, using 50 kGy radiation and 10, 15, or 20 wt/vol % VDM solutions as listed in Table 20 below. Although a significant amount of poly(VDM) was grafted to the membranes, it is apparent from measurements of physical properties that no significant change in the physical porous properties occurred. Most importantly, flow properties were not diminished beyond continued usefulness of the azlactone-functional membranes.

TABLE 20

POROUS PROPERTIES OF DISPERSION POLYMERIZED SAMPLES

| Example | VDM Conc. (wt/vol %) | Wt. % Add-On | Thickness (μm) | Pore Size (μm) | Gurley Wt. (sec/50 cc) | Porosity (%) | Water Permability (ml/mn/cm² @ 10 psi) |
|---|---|---|---|---|---|---|---|
| 66 | 0 | 0.0 | 51 | 0.54 | 22 | 67.5 | 3.68 |
| 67 | 10 | 10.1 | 52 | 0.59 | 21 | 65.9 | 2.91 |
| 68 | 15 | 13.3 | 51 | 0.56 | 23 | 66.3 | 3.12 |
| 69 | 20 | 15.2 | 47 | 0.55 | 22 | 66.2 | 1.60 |

The samples of Examples 66–69 were also tested for ability to couple protein A according to the method of Example 5 above. The protein was dissolved in either a $SO_4$ or a PBS buffer system as used in Examples 63–65. Table 21 shows the results below.

TABLE 21

PROTEIN BINDING PROPERTIES OF GRAFTED SAMPLES

| Example | IR Ratio* (wt/vol 5) | Wt Add On (%) | Buffer Type | Protein Binding (μg/cm²) | SDS Res. (%) | Protein Coupling (μg/cm²) |
|---|---|---|---|---|---|---|
| 66 | 0.000 | 0.0 | $SO_4$ | 18.3 | 31.4 | 5.7 |
| 67 | 0.543 | 10.1 | $SO_4$ | 33.2 | 94.3 | 31.3 |
| 68 | 0.691 | 13.3 | $SO_4$ | 29.5 | 94.8 | 27.8 |
| 69 | 0.662 | 15.2 | $SO_4$ | 32.6 | 94.1 | 30.6 |
| 66 | 0.000 | 0.0 | PBS | 17.8 | 29.9 | 4.3 |
| 67 | 0.543 | 10.1 | PBS | 8.9 | 84.4 | 7.6 |
| 68 | 0.691 | 13.3 | PBS | 8.1 | 75.9 | 6.1 |
| 69 | 0.662 | 15.2 | PBS | 6.3 | 85.1 | 5.4 |

*Ratio of the azlactone absorbance of 1824 cm$^{-1}$ to that of the PE at 1462 cm$^{-1}$ These data show that the addition of azlactone functionality does correlate with an increase in coupled protein. Also, the $SO_4$ buffer system was preferred.

Samples of Example 67 were also tested for rate of binding during incubation binding and flow-through binding techniques in the same manner as used for Example 63 above. For the incubation binding technique, the amount of initial binding ranged from 21.8 μg/cm² for 0.5 hours incubation to 37.4 μg/cm² for 16 hours of incubation. For the flow-through binding technique, the amount of initial binding was an average of 20.4 μg/ml for a flow-through exposure of about 3 minutes. As with Example 63, flow-through binding techniques

What is claimed is:

1. An adduct support, comprising: a chemically reactive support having azlactone-functionality at surfaces of the support and a ligand comprising a nucleophilic reagent reacted with the azlactone-functionality, wherein the chemically reactive support comprises a porous pre-existing support having surfaces and azlactone-functional moieties contacting only the surfaces and modifying reactivity of only such surfaces while retaining useful porosity of the pre-existing support;

wherein said contacting is selected from the group consisting of chemically grafting the azlactone-functional moieties to the surfaces, crosslinking the azlactone-functional moieties in a coating over the surfaces, and forming crosslinked particles of the azlactone-functional moieties in contact with the surfaces.

2. The adduct support according to claim 1, wherein the azlactone-functional moieties comprise oxazolinone moieties of the formula:

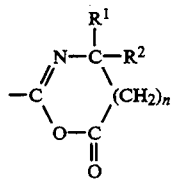

wherein $R^1$ and $R^2$ independently can be an alkyl group having 1 to 14 carbon atoms, a cycloalkyl group having 3 to 14 carbon atoms, an aryl group having 5 to 12 ring atoms, an arenyl group having 6 to 26 carbon atoms and 0 to 3 S, N, and nonperoxidic O heteroatoms, or $R^1$ and $R^2$ taken together with the carbon to which they are joined can form a carbocyclic ring containing 4 to 12 ring atoms, and n is an integer 0 or 1.

3. The adduct support according to claim 1, wherein the pre-existing support is a ceramic, glassy, metallic, or polymeric material.

4. The adduct support according to claim 3, wherein the pre-existing support is a polymeric material.

5. The adduct support according to claim 4, wherein the porous, polymeric material is a woven web, a nonwoven web, a microporous fiber, or a microporous membrane.

6. The adduct support according to claim 1, wherein the nucleophilic reagent comprises biologically active materials, acids, bases, chelators, hydrophiles, lipophiles, hydrophobes, zwitterions, detergents, or combinations thereof.

7. The adduct support according to claim 6, wherein biologically active material comprises substances which are biologically, immunochemically, physiologically, or pharmaceutically active.

8. The adduct support according to claim 7, wherein the biologically active material comprises proteins, peptides, polypeptides, antibodies, antigenic substances, enzymes, cofactors, inhibitors, lectins, hormones, receptors, coagulation factors, amino acids, histones, vitamins, drugs, cell surface markers, substances which interact with them, or combinations thereof.

9. The adduct support according to claim 6, wherein the adduct support is an adsorbant, complexing agent, catalyst, or chromatographic article.

10. The adduct support according to claim 6, wherein the adduct support is a mammalian body implant and wherein the nucleophilic reagent is an anticoagulant.

* * * * *